(12) United States Patent
Hagen et al.

(10) Patent No.: US 7,304,050 B2
(45) Date of Patent: Dec. 4, 2007

(54) ANTIBACTERIAL AGENTS

(75) Inventors: Susan Hagen, Canton, MI (US); Vara Prasad Venkata Nagendra Josyula, Ann Arbor, MI (US)

(73) Assignee: Pfizer Inc., New York, NY (US)

( * ) Notice: Subject to any disclaimer, the term of this patent is extended or adjusted under 35 U.S.C. 154(b) by 363 days.

(21) Appl. No.: 10/931,400

(22) Filed: Sep. 1, 2004

(65) Prior Publication Data

US 2005/0070523 A1    Mar. 31, 2005

Related U.S. Application Data

(60) Provisional application No. 60/503,415, filed on Sep. 16, 2003.

(51) Int. Cl.
*A61P 31/04* (2006.01)
*A61K 31/55* (2006.01)
*C07D 223/16* (2006.01)

(52) U.S. Cl. .......................... 514/213.01; 514/217.01; 540/593; 540/594

(58) Field of Classification Search ........... 514/213.01, 514/217.01; 540/593, 594
See application file for complete search history.

(56) References Cited

U.S. PATENT DOCUMENTS

| | | | |
|---|---|---|---|
| 4,705,799 A | 11/1987 | Gregory | 514/376 |
| 5,043,443 A | 8/1991 | Carlson et al. | 544/112 |
| 5,164,510 A | 11/1992 | Brickner | 548/231 |
| 5,182,403 A | 1/1993 | Brickner | 548/231 |
| 5,225,565 A | 7/1993 | Brickner | 548/229 |
| 5,231,188 A | 7/1993 | Brickner | 548/221 |
| 5,247,090 A | 9/1993 | Brickner | 546/89 |
| 5,523,403 A | 6/1996 | Barbachyn | 544/137 |
| 5,529,998 A | 6/1996 | Habich et al. | 514/233.8 |
| 5,547,950 A | 8/1996 | Hutchinson et al. | 514/252 |
| 5,565,571 A | 10/1996 | Barbachyn et al. | 546/144 |
| 5,614,535 A | 3/1997 | Juraszyk et al. | 514/326 |
| 5,627,181 A | 5/1997 | Riedl et al. | 514/236.8 |
| 5,652,238 A | 7/1997 | Brickner et al. | 514/235.8 |
| 5,684,023 A | 11/1997 | Riedl et al. | 514/337 |
| 5,688,792 A | 11/1997 | Barbachyn et al. | 514/235.5 |
| 5,698,574 A | 12/1997 | Riedl et al. | 514/376 |
| 5,792,765 A | 8/1998 | Riedl et al. | 514/236.8 |
| 5,827,857 A | 10/1998 | Riedl et al. | 514/301 |
| 5,843,967 A | 12/1998 | Riedl et al. | 514/340 |
| 5,861,413 A | 1/1999 | Habich et al. | 514/312 |
| 5,869,659 A | 2/1999 | Stolle et al. | 544/114 |
| 5,952,324 A | 9/1999 | Barbachyn et al. | 514/211 |
| 5,968,962 A | 10/1999 | Thomas et al. | 514/376 |
| 5,981,528 A | 11/1999 | Gravestock | 514/252 |
| 5,990,136 A | 11/1999 | Barbachyn et al. | 514/340 |
| 6,043,266 A | 3/2000 | Ennis et al. | 514/376 |
| 6,051,716 A | 4/2000 | Hutchinson et al. | 548/229 |
| 6,069,145 A | 5/2000 | Betts | 514/252 |
| 6,069,160 A | 5/2000 | Stolle et al. | 514/367 |
| 6,110,936 A | 8/2000 | Gravestock | 514/315 |
| 6,166,056 A | 12/2000 | Thomas et al. | 514/376 |
| 6,194,441 B1 | 2/2001 | Roberts et al. | 514/340 |
| 6,239,152 B1 | 5/2001 | Gordeev et al. | 514/340 |
| 6,239,283 B1 | 5/2001 | Gage | 548/225 |
| 6,271,383 B1 | 8/2001 | Gravestock | 546/209 |
| 6,313,307 B1 | 11/2001 | Ennis et al. | 548/229 |
| 6,689,769 B2 | 2/2004 | Gordeev et al. | 514/183 |

FOREIGN PATENT DOCUMENTS

| | | |
|---|---|---|
| DE | 19805117 | 8/1999 |
| DE | 19901306 | 7/2000 |
| DE | 19905278 | 8/2000 |
| EP | 0417044 A2 | 8/1990 |
| EP | 0697408 B1 | 8/1995 |
| JP | 03181478 A | 8/1991 |
| WO | WO94/01110 | 1/1994 |
| WO | WO95/07271 | 3/1995 |
| WO | WO95/25106 | 9/1995 |
| WO | WO96/13502 | 5/1996 |
| WO | WO96/15130 | 5/1996 |
| WO | WO96/23788 | 8/1996 |
| WO | WO96/35691 | 11/1996 |
| WO | WO97/09328 | 3/1997 |
| WO | WO97/30995 | 8/1997 |
| WO | WO98/54161 | 12/1998 |
| WO | WO99/03846 | 1/1999 |
| WO | WO99/29688 | 6/1999 |
| WO | WO99/37641 | 7/1999 |
| WO | WO99/37652 | 7/1999 |
| WO | WO99/40094 | 8/1999 |
| WO | WO99/64417 | 12/1999 |
| WO | WO 00/10566 A1 | 3/2000 |
| WO | WO00/21960 | 4/2000 |
| WO | WO00/44741 | 8/2000 |
| WO | WO00/73301 | 12/2000 |
| WO | WO01/40236 | 6/2001 |
| WO | WO01/46185 | 6/2001 |
| WO | WO01/81350 | 11/2001 |
| WO | WO 02/059115 A1 | 8/2002 |

(Continued)

OTHER PUBLICATIONS

Abdelaal, et. al., "Synthesis of 1-[3-Methyl]-2(3H)-benzazolon-5- or 6-yl]-4-{4-[cis-2-(2,4-dichlorophenyl)-2-(1H-imidazol-1-yl-methyl)-1,3-dioxolan-4-yl]methyleneoxyphenyl]}piperazines" Journal of Heterocyclic Chem., 29, 1069, (1992).

(Continued)

*Primary Examiner*—Brenda Coleman
(74) *Attorney, Agent, or Firm*—Steve T. Zelson; Jason G. Tebbutt

(57) ABSTRACT

Compounds of formula I and methods for their preparation are disclosed. Further disclosed are methods of making biologically active compounds of formula I as well as pharmaceutically acceptable compositions comprising compounds of formula I. Compounds of formula I as disclosed herein can be used in a variety of applications, including using the invention compounds to treat bacterial infections.

5 Claims, No Drawings

FOREIGN PATENT DOCUMENTS

| WO | WO02/059155 | 8/2002 |
|---|---|---|
| WO | WO02/096916 | 12/2002 |
| WO | WO03/006440 | 1/2003 |
| WO | WO02/059116 | 8/2003 |

OTHER PUBLICATIONS

Barbachyn, et. al. "Identification of a Novel Oxazolidinone (U-100480) with Potent Antimycobacterial Activity." Journal of Medicinal Chemistry. 1996, 39, 680-685.

Blache, et. al. "Application of the Mercuric Acetate-Edetic Acid Oxidation Method To The Synthesis of 11-Aza-1,2,3,4,5,6,7,12bpOctahydroindolo[2,3-a]Quinolizines." Heterocycles, vol. 45, No. 1, pp. 57-69, 1997.

Bodor, Nicholas and J. Hillis Miller, "Novel Approaches in Prodrug Design." Drugs of the Future vol. VI, No. 3, 1981, pp. 165-182.

Brickner, Steven J. "Oxazolidinone Antibacterial Agents." Current Pharmaceutical Design. 1996, 2, 175-194.

Brickner, et. al. "Synthesis and Antibacterial Activity of U-100592 and U-100766, Two Oxazolidinone Antibacterial Agents for the Potential Treatment of Multidrug-Resistant Gram-Positive Bacterial Infections." Journal of Medicinal Chemistry. 1996, 39, 673-679.

Bundgaard, Hans. "Design of prodrugs: Bioreversible derivatives for various functional groups and chemical entities." Design of Prodrugs, Chapter 1, 1985.

Cava, Michael P. and Matthew I. Levinson. "Thionation Reactions of Lawesson's Reagents." Tetrahedron vol. 41, No. 22, pp. 5061-5087, 1985.

Clark, Robert L. and Arsenio A. Pessolano. "Synthesis of Some Substituted Benzoxazolones." Journal of the American Chemical Society. vol. 80, pp. 1662, 1958.

Comins, et. al. "Preparation of 2,6-Disubstituted 2,3-Dihydro-4-pyridones: Dehydrogenation of Trimethylsilyl Enol Ethers with Palladium (II) Acetate." Tetrahedron Letters, vol. 36, No. 52, pp. 9449-9452, 1995.

Comins, et. al. "Regio- and Stereoselective Addition of Nucleophiles to 1-Phenoxycarbonyl-2,3-Dihydropyridium Salts." Heterocycles, vol. 37, No. 2, 1994, pp. 1121-1140.

Dehmlow, Eckehard, and Ralf Westerheide. "Studies Towards 3,4-Dimethoxy-1-Methyl-1,2-Dihydropyridine, so-called Arecolidine, or its Tautomers." Heterocycles, vol. 37, No. 1, 1994, pp. 355-366.

Diez, et. al. "Preparation of a New Chiral 5,6-Dihydropyridinium Synthon." Heterocycles, vol. 31, No. 3, 1990, pp. 485-492.

Dodd, Dharmpal and Allan Oehlschlager. "Efficient Route to the Synthesis of C-2, C-3 Substituted 4-Piperidones." Tetrahedron Letters, vol. 32, No. 30, pp. 3643-3646, 1991.

Evans, et. al. "Regioselective Preparation of a,B-Unsaturated Ketones via the Direct Dehydrogeantion of Triisopropylsilyl Enol Ethers." Tetrahedron Letters, vol. 36, No. 23, pp. 3985-3988, 1995.

Gage, et. al. "Stereodivergent synthesis of sulfoxide-containing oxazolidinone antibiotics." Tetrahedron Letters, 41 (2000) 4301-4305.

Guerry Philippe and Reinhard Neier, "Photochemical Cycloadditions to 5,6-Dihydro-4-pyridones." Chimia 41 (1987) No. 10 (October), pp. 341-342.

Guerry, Philippe and Reinhard Neier. "Reduktion von 4-Pyridinonen." Synthesis, Jun. 1984 pp. 485-488.

Haider, et. al. "140. Synthesis of 4-Oxo-1,2,3,4-tetrahydropyridine (2,3-Dihydro-4(1H)pyridinone)." Helvetica Chimica Acta—vol. 58, Fasc. 5 (1975)—Nr. 139-140 pp. 1287-1292.

Herrinton, et. al. "Iodination and Metal Halogen Exchange of Aromatic Compounds: An Improved Preparation of a Key Oxazolidinone Antibiotic Intermediate." Organic Process Research and Development 2001, 5, 80-83.

Ishii, et. al. "Rhodium-Catalyzed Reaction of N-Acylpiperazines with CO and Ethylene, Carbonylation at a C-H Bond Directed by an Amido Group." Tetrahedron Letters, vol. 38, No. 43, pp. 7565-7568, 1997.

Kirschbaum, Stephen, and Herbert Waldmann. "Construction of the Tricyclic Benzoquinolizine Ring System by Combination of a Tandem Mannich-Michael Reaction with a Heck Reaction." Tetrahedron Letters, vol. 38, No. 16, pp. 2829-2832, 1997.

Kirschbaum, Stepen, and Herbert waldmann. "Three-Step Access to the Tricyclic Benzo[a]quinolizine Ring System." Journal of Organic Chemistry. 1998, 63, 4936-4946.

Lock, Ralf, and Herbert Waldmann. "Asymetric Synthesis of Highly Functionalized Tetracyclic Indole Bases Embodying the Basic Skeleton of Yohimbinep and Reserpine Type Alkaloids." Tetrahedron Letters, vol. 37, No. 16, pp. 2753-2756, 1996.

Lock, Ralf, and Herbert Waldmann. "Enantioselective Construction of Highly Fuctionalized Indoloquinolizines Congeners to Polycyclic Indole Alkaloids." Chem. Eur. J. 1997, 3, No. 1, pp. 143-151.

Mai, et. al. "N-[4-(1,1'-Biphenylyl)Methyl]-4-(4-Thiomorpholinylmethyl) Benzenamines, a New Class of Synthetic Antituberculosis Agents Active Against Mycobacterium Avium." Medicinal Chemistry Research, 9:3 (1999) 149-161.

Notari, Robert E., "Theory and Practice of Prodrug Kinetics." Methods in Enzymology, vol. 112, 1985, pp. 309-323.

Reggelin, Michael, and Cornelia Zur, "Sulfoximines; Structures, Properties and Synthetic Applications." Synthesis, 2000, No. 1, 1-64.

Roush, William R., and Bradley B. Brown. "Enantioselective Syntehsis of 2-Alkyl-5-methylene-1,3-dioxolan-4-ones and Exo-Selective Diels-Alder Reactions with Cyclopentadiene." Journal of Organic Chemistry. 1992, 57, 3380-3387.

Stutz, P, and PA Stadler, "A Novel Approach to Cyclic b-Carbonyl-Enamines 7,8—Lysergic Acid Derivatives Via The Polonovski Reaction." Tetrahedron Letters No. 51, pp. 5095-5098, 1973.

Waldmann et. al. "Asymmetric Synthesis of Indolo[2,3-a]quinolizidin-2-onesCongeners to Yohimbine-Type Alkaloids." Tetrahedron vol. 49, No. 2, 1993, pp. 397-416.

Yamamoto, Yutaka, and Akihiko Yanagi. "Studies on Organometallic Compounds, II Facile and Convenient Method for the Synthesis of Iodoazines through Iododestannation of Trimethylstannylazines." Chem Pharm. Bull. 30(5) 1731-1737(1982).

English Abstract of article, Guerry, Philippe and Reinhard Neier. "Reduktion von 4-Pyridinonen." Synthesis, Jun. 1984 pp. 485-488.

English Abstract of EP0417044A2, 1990.

English Abstract of Patent DE19901306, 2000.

English Abstract of Patent DE19805117, 1999.

English Abstract of Patent DE19905278, 2000.

Cecchetti V, et al., "Chemometric methodologies in a quantitative structure—activity relationship study: the antibacterial activity of 6-aminoquinolones", Journal of Medicinal Chemistry, 1997, vol. 40, pp. 1698-1706.

Cecchetti V, et al., "Studies on 6-aminoquinolones: synthesis and antibacterial evaluation of 6-amino-8-methyquinolones", Journal of Medicinal Chemistry, 1996. vol. 39, No. 2, pp. 436-445.

Johnson P D, et al., "Synthesis and Biological Evaluation of Benzazepine Oxazolidinone Antibacterials", Bioorganic & Medicinal Chemistry Letters, Dec. 1, 2003 vol. 13, No. 23, pp. 4197-4200.

English Abstract of Patent JP 03181478 A, 1991.

ANTIBACTERIAL AGENTS

CROSS REFERENCE TO RELATED APPLICATION

This application claims the benefit of U.S. Provisional Application Ser. No. 60/503,415, filed Sep. 16, 2003, the contents of which are hereby incorporated by reference.

FIELD OF THE INVENTION

The invention relates to compounds bearing an oxazolidinone core structure which exhibit antibacterial activity, methods for their preparation, as well as pharmaceutically acceptable compositions comprising such compounds.

BACKGROUND OF THE INVENTION

The quinones and oxazolidinones are novel classes of antibacterial agents with potent activity against a number of human and veterinary pathogens. However, bacterial resistance to compounds within each of theses classes has been observed. As a result, there is a need for new antibacterial agents that possess the activity profiles of the oxazolidinones and quinones, and yet are active against resistant bacterial strains. A potential drug development strategy that addresses this need is aimed at combining key oxazolidinone and quinone structural motifs in one molecule, thus providing a quinone-oxazolidinone ("quin-ox") antibacterial hybrid.

SUMMARY OF THE INVENTION

These and other needs are met by the present invention, which is directed to a compound of formula I:

or a pharmaceutically acceptable salt thereof wherein
A is O,
  NH, or
  S;
B is
  $C(=O)R_a$,
  $C(=S)R_a$,
  heterocylco,
  heteroaryl,
  $C(=O)$-heterocyclo,
  $C(=N)$—CN, or
  $C(=O)$—heteteroaryl;
either D is N, E is C, and F is CH when "..." is a bond, or D is CH, E is N, and F is $CH_2$ when "..." is absent;
J, K, Q independently are $CR_b$ or N, with the proviso that when any one of J, K, or Q is N, then the other two are $CR_b$;
"..." are each independently absent; or are bonds;
$R_a$ is H,
  $(C_1-C_8)$alkyl,
  $(C_3-C_6)$cycloalkyl,
  O—$(C_1-C_4)$alkyl,
  O—$(C_3-C_6)$cycloalkyl,
  S—$(C_1-C_4)$ alkyl,
  S—$(C_3-C_6)$cycloalkyl,
  $NH_2$,
  $NH(C_1-C_4)$alkyl,
  $N((C_1-C_4)alkyl)_2$, or
  NH—$(C_3-C_6)$cycloalkyl,
$R_b$ is H;
  halo,
  $(C_1-C_8)$alkyl,
  $(C_3-C_6)$cycloalkyl,
  O—$(C_1-C_4)$alkyl,
  O—$(C_3-C_6)$cycloalkyl,
  S—$(C_1-C_4)$ alkyl,
  S—$(C_3-C_6)$cycloalkyl,
  $NH_2$,
  $NH(C_1-C_4)$alkyl,
  $N((C_1-C_4)alkyl)_2$, or
  NH—$(C_3-C_6)$cycloalkyl;
n is 0, 1, or 2;
at least one of W, X, or Y is NP and the other two are each independently absent,
  —$CH_2$—,
  —$CH_2$—$CH_2$—, or
  —C=C—;
P is wherein

"∿∿∿"

indicates the point of attachment,
Z is N or C, provided that when Z is N, $R_5$ is absent at that position;
$R_1$ is $(C_1-C_6)$alkyl,
  halo$(C_1-C_6)$alkyl,
  $(C_3-C_6)$cycloalkyl,
  halo$(C_3-C_6)$cycloalkyl,
  aryl, and
  heteroaryl;
$R_2$ is OH,
  $O(C_1-C_6)$alkyl,
  $O(C_3-C_6)$cycloalkyl, O—$(CHR_{2a})_m$—O—$\overset{O}{\underset{\|}{C}}$—$QR_{2b}$, wherein m is an integer of from 1 to 10, Q is O or is absent, and $R_{2a}$ is H or $(C_1-C_6)$alkyl and $R_{2b}$ is $(C_1-C_6)$alkyl, aryl, or heteroaryl, O—$(CHR_{2a})_n$—Y, wherein $R_{2a}$ is as defined above, n is an integer of from 2 to 10, Y is OH or $NR_{2c}R_{2d}$, wherein $R_{2c}$ and $R_{2d}$ are each independently H, $(C_1-C_6)$alkyl, or $(C_3-C_6)$cycloalkyl, or $NR_{2d}$, wherein $R_{2d}$ is as defined above,

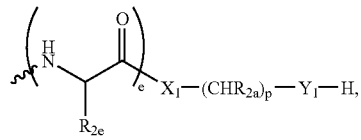

wherein

"~~~"

indicates the point of attachment, 2a is as defined above, $R_{2e}$ is H or $(C_1-C_6)$alkyl, e is an integer of from 1 to 10, p is an integer of from 2 to 10, and $X_1$ and $Y_1$ are each independently NH or O;

$R_3$, $R_4$, and $R_5$ are each independently H, halo, $NH_2$, $(C_1-C_6)$alkyl, halo$(C_1-C_6)$alkyl, $(C_1-C_6)$alkoxy, or halo$(C_1-C_6)$alkoxy; or $R_1$, and $R_5$, together with the carbons to which they are attached, are joined to form a 6-membered substituted or unsubstituted ring containing 1 or 2 heteroatroms selected from NH, $N(C_1-C_6)$alkyl, or O.

The invention is also directed to a compound which is

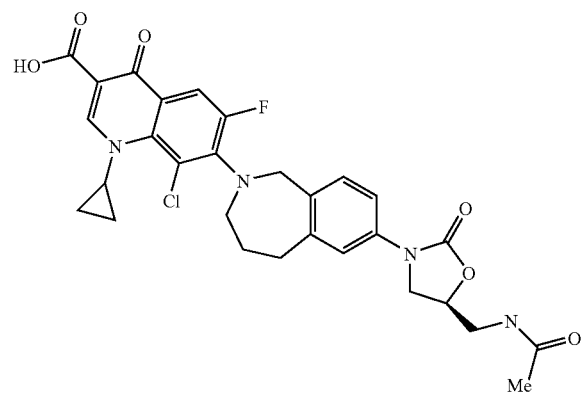

7-{7-[5-(Acetylamino-methyl)-2-oxo-oxazolidin-3-yl]-1,3,4,5-tetrahydro-benzo[c]azepin-2-yl}-8-chloro-1-cyclopropyl-6-fluoro-4-oxo-1,4-dihydro-quinoline-3-carboxylic acid;

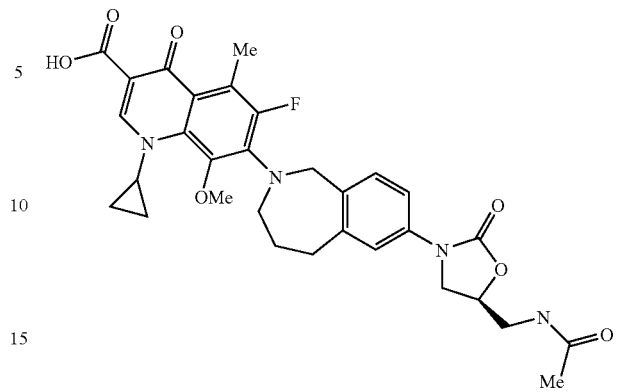

7-{7-[5-(Acetylamino-methyl)-2-oxo-oxazolidin-3-yl]-1,3,4,5-tetrahydro-benzo[c]azepin-2-yl}-1-cyclopropyl-6-fluoro-8-methoxy-5-methyl-4-oxo-1,4-dihydro-quinoline-3-carboxylic acid;

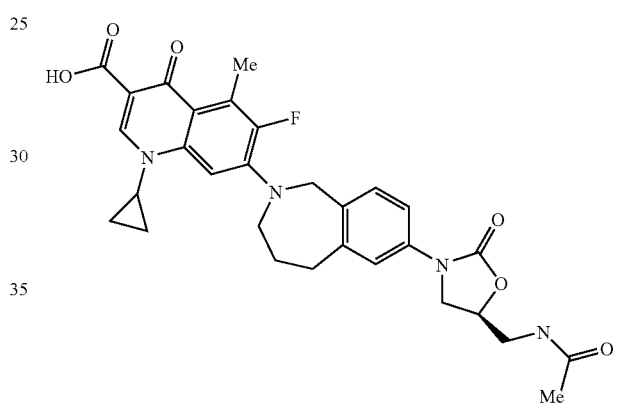

7-{7-[5-(Acetylamino-methyl)-2-oxo-oxazolidin-3-yl]-1,3,4,5-tetrahydro-benzo[c]azepin-2-yl}-1-cyclopropyl-6-fluoro-5-methyl-4-oxo-1,4-dihydro-quinoline-3-carboxylic acid;

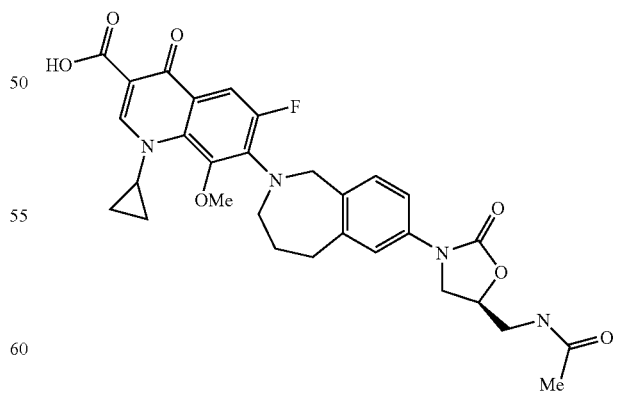

7-{7-[5-(Acetylamino-methyl)-2-oxo-oxazolidin-3-yl]-1,3,4,5-tetrahydro-benzo[c]azepin-2-yl}-1-cyclopropyl-6-fluoro-8-methoxy-4-oxo-1,4-dihydro-quinoline-3-carboxylic acid;

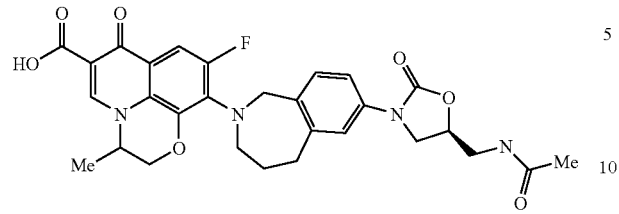

9-{7-[5-(Acetylamino-methyl)-2-oxo-oxazolidin-3-yl]-1,3,4,5-tetrahydro-benzo[c]azepin-2-yl}-8-fluoro-3-methyl-6-oxo-2,3-dihydro-6H-1-oxa-3a-aza-phenalene-5-carboxylic acid;

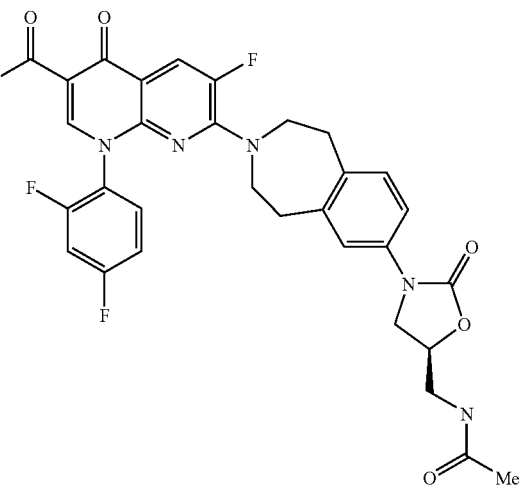

7-{7-[5-(Acetylamino-methyl)-2-oxo-oxazolidin-3-yl]-1,2,4,5-tetrahydro-benzo[d]azepin-3-yl}-1-(2,4-difluoro-phenyl)-6-fluoro-4-oxo-1,4-dihydro-[1,8]naphthyridine-3-carboxylic acid;

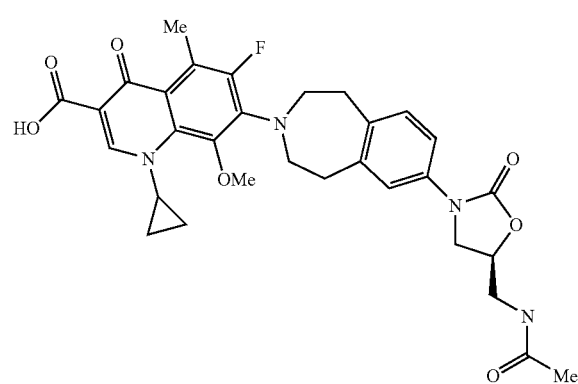

7-{7-[5-(Acetylamino-methyl)-2-oxo-oxazolidin-3-yl]-1,2,4,5-tetrahydro-benzo[d]azepin-3-yl}-1-cyclopropyl-6-fluoro-8-methoxy-5-methyl-4-oxo-1,4-dihydro-quinoline-3-carboxylic acid;

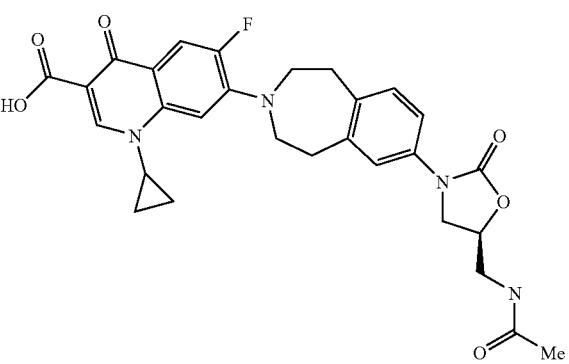

7-{7-[5-(Acetylamino-methyl)-2-oxo-oxazolidin-3-yl]-1,2,4,5-tetrahydro-benzo[d]azepin-3-yl}-1-cyclopropyl-6-fluoro-4-oxo-1,4-dihydro-quinoline-3-carboxylic acid;

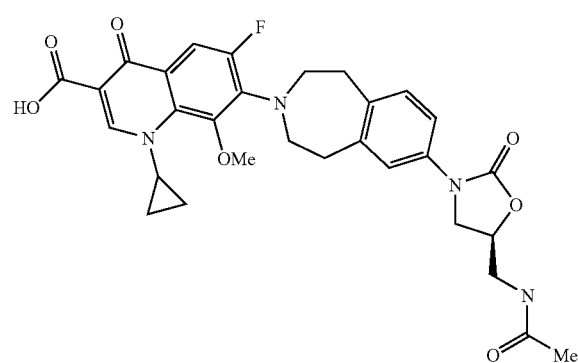

7-{7-[5-(Acetylamino-methyl)-2-oxo-oxazolidin-3-yl]-1,2,4,5-tetrahydro-benzo[d]azepin-3-yl}-1-cyclopropyl-6-fluoro-8-methoxy-4-oxo-1,4-dihydro-quinoline-3-carboxylic acid;

7-{7-[5-(Acetylamino-methyl)-2-oxo-oxazolidin-3-yl]-1,2,4,5-tetrahydro-benzo[d]azepin-3-yl}-8-chloro-1-cyclopropyl-6-fluoro-4-oxo-1,4-dihydro-quinoline-3-carboxylic acid;

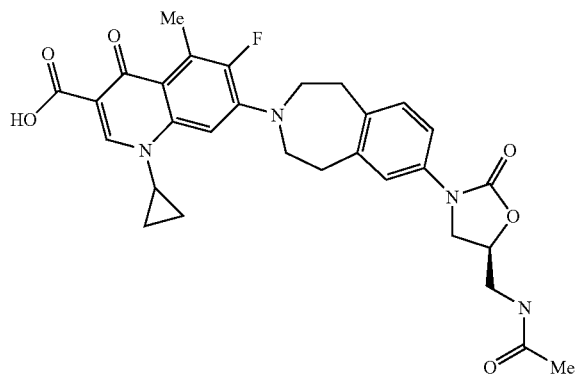

7-{7-[5-(Acetylamino-methyl)-2-oxo-oxazolidin-3-yl]-1,2,
4,5-tetrahydro-benzo[d]3-yl}-1-cyclopropyl-6-fluoro-5-methyl 4-oxo-1,4-dihydro-quinoline-3-carboxylic acid;

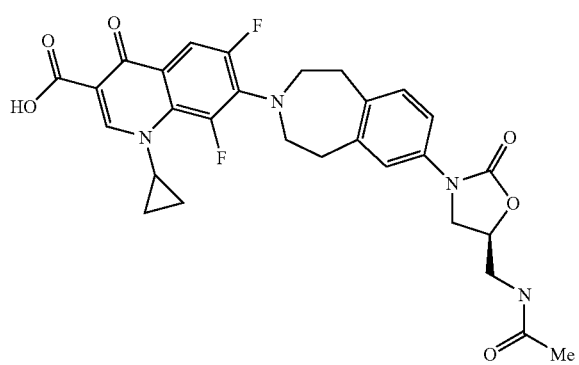

7-{7-[5-(Acetylamino-methyl)-2-oxo-oxazolidin-3-yl]-1,2,
4,5-tetrahydro-benzo[d]azepin-3-yl}-1-cyclopropyl-6,8-difluoro-4-oxo-1,4-dihydro-quinoline-3-carboxylic acid;

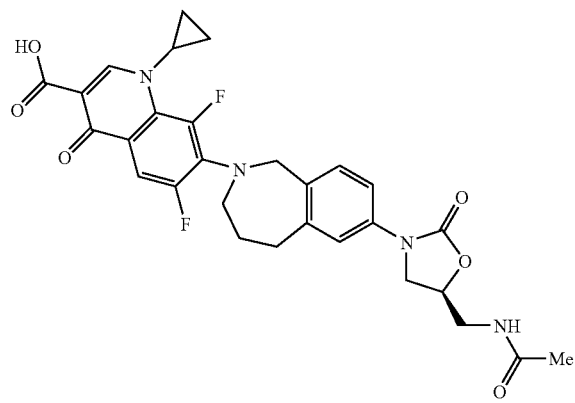

7-{7-[5-(Acetylamino-methyl)-2-oxo-oxazolidin-3-yl]-1,3,
4,5-tetrahydro-benzo[c]azepin-2-yl}-1-cyclopropyl-6,8-difluoro-4-oxo-1,4-dihydro-quinoline-3-carboxylic acid;

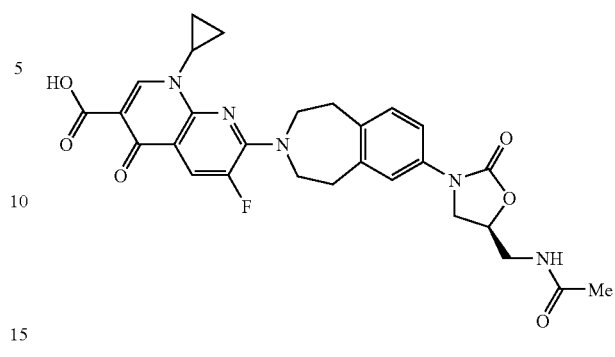

7-{7-[5-(Acetylamino-methyl)-2-oxo-oxazolidin-3-yl]-1,2,
4,5-tetrahydro-benzo[d]azepin-3-yl}-1-cyclopropyl-6-fluoro-4-oxo-1,4-dihydro-[1,8]naphthyridine-3-carboxylic acid;

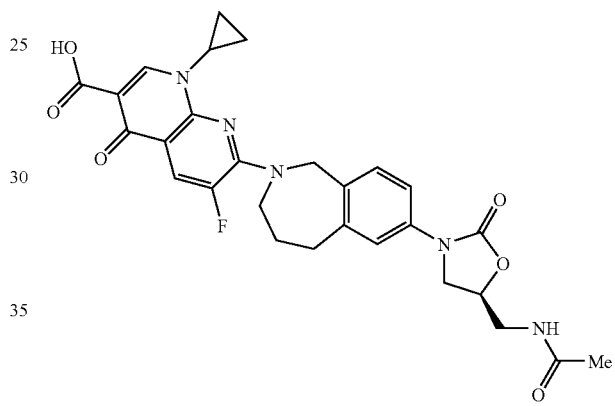

7-{7-[5-(Acetylamino-methyl)-2-oxo-oxazolidin-3-yl]-1,3,
4,5-tetrahydro-benzo[c]azepin-2-yl}-1-cyclopropyl-6-fluoro-4-oxo-1,4-dihydro-[1,8]naphthyridine-3-carboxylic acid;

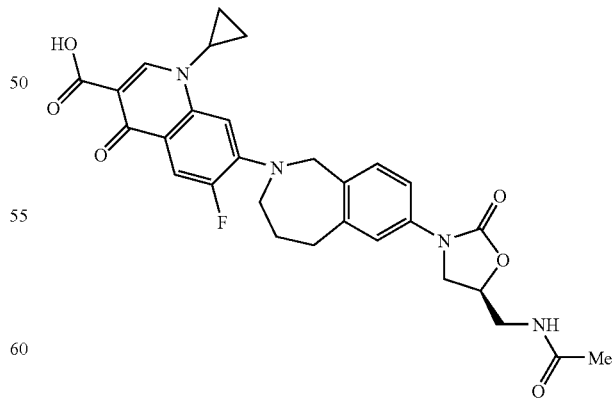

7-{7-[5-(Acetylamino-methyl)-2-oxo-oxazolidin-3-yl]-1,3,
4,5-tetrahydro-benzo[c]azepin-2-yl}-1-cyclopropyl-6-fluoro-4-oxo-1,4-dihydro-quinoline-3-carboxylic acid;

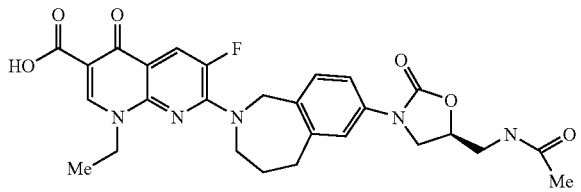

7-{7-[5-(Acetylamino-methyl)-2-oxo-oxazolidin-3-yl]-1,3,4,5-tetrahydro-benzo[c]azepin-2-yl}-1-ethyl-6-fluoro-4-oxo-1,4-dihydro-[1,8]naphthyridine-3-carboxylic acid; or

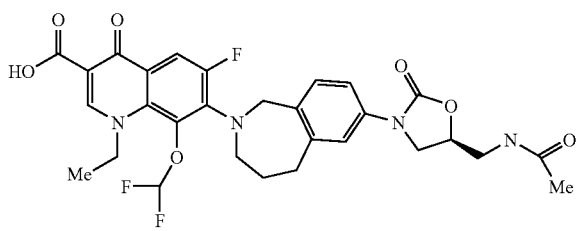

7-{7-[5-(Acetylamino-methyl)-2-oxo-oxazolidin-3-yl]-1,3,4,5-tetrahydro-benzo[c]azepin-2-yl}-1-cyclopropyl-8-difluoromethoxy-6-fluoro-4-oxo-1,4-dihydro-[1,8]naphthyridine-3-carboxylic acid.

The invention is also directed to a compound of formula II

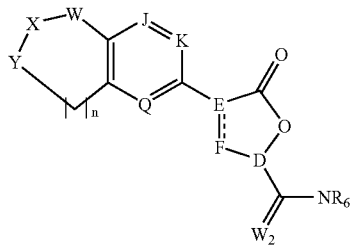

II or a pharmaceutically acceptable salt thereof wherein
$W_2$ is O or S;
either D is N, E is C, and F is CH when "..." is a bond, or D is CH, E is N, and F is $CH_2$ when "..." is absent;
J, K, Q independently are $CR_b$ or N, with the proviso that when any one of J, K, or Q is N, then the other two are $CR_b$;
"..." are each independently absent; or are bonds;
$R_a$ is H,
$(C_1-C_8)$alkyl,
$(C_3-C_6)$cycloalkyl,
O—$(C_1-C_4)$alkyl,
O—$(C_3-C_6)$cycloalkyl,
S—$(C_1-C_4)$ alkyl,
S—$(C_3-C_6)$cycloalkyl,
$NH_2$,
$NH(C_1-C_4)$alkyl,
$N((C_1-C_4)$alkyl$)_2$, or
NH—$(C_3-C_6)$cycloalkyl, $R_b$ is H;
halo,
$(C_1-C_8)$alkyl,
$(C_3-C_6)$cycloalkyl,
O—$(C_1-C_4)$alkyl,
O—$(C_3-C_6)$cycloalkyl,
S—$(C_1-C_4)$ alkyl,
S—$(C_3-C_6)$cycloalkyl,
$NH_2$,
$NH(C_1-C_4)$alkyl,
$N((C_1-C_4)$alkyl$)_2$, or
NH—$(C_3-C_6)$cycloalkyl;
n is 0, 1, or 2;
at least one of W, X, or Y is NP and the other two are each independently absent,
—$CH_2$—,
—$CH_2$—$CH_2$—, or
—C≡C—;
P is

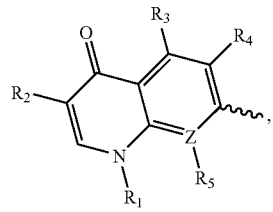

wherein

"〜〜〜"

indicates the point of attachment,
Z is N or C, provided that when Z is N, $R_5$ is absent at that position;
$R_1$ is $(C_1-C_6)$alkyl,
halo$(C_1-C_6)$alkyl,
$(C_3-C_6)$cycloalkyl,
halo$(C_3-C_6)$cycloalkyl,
aryl, and
heteroaryl;
$R_2$ is OH,
$O(C_1-C_6)$alkyl,
$O(C_3-C_6)$cycloalkyl,

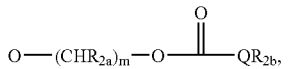

wherein m is an integer of from 1 to 10, Q is O or is absent, and $R_{2a}$ is H or $(C_1-C_6)$alkyl and $R_{2b}$ is $(C_1-C_6)$alkyl, aryl, or heteroaryl,
O—$(CHR_{2a})_n$—Y, wherein $R_{2a}$ is defined above, n is an integer of from 2 to 10, Y is OH or $NR_{2c}R_{2d}$, wherein $R_{2c}$ and $R_{2d}$ are each independently H, $(C_1-C_6)$alkyl, or $(C_3-C_6)$cycloalkyl, or
$NR_{2d}$, wherein $R_{2d}$ is as defined above,

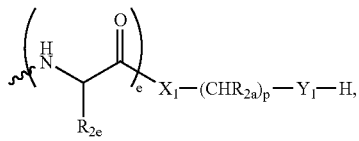

wherein

"⌇⌇⌇"

indicates the point of attachment, 2a is as defined above, $R_{2e}$ is H or $(C_1\text{-}C_6)$alkyl, e is an integer of from 1 to 10, p is an integer of from 2 to 10, and $X_1$ and $Y_1$ are each independently NH or O;

$R_3$, $R_4$, and $R_5$ are each independently H,
halo,
$NH_2$,
$(C_1\text{-}C_6)$alkyl,
halo$(C_1\text{-}C_6)$alkyl,
$(C_1\text{-}C_6)$alkoxy, or
halo$(C_1\text{-}C_6)$alkoxy; or $R_1$, and $R_5$, together with the carbons to which they are attached, are joined to form a 6-membered substituted or unsubstituted ring containing 1 or 2 heteroatroms selected from NH, $N(C_1\text{-}C_6)$alkyl, or O; and $R_6$ is H,
OH,
$(C_1\text{-}C_6)$alkyl,
$(C_3\text{-}C_6)$cycloalkyl,
$(C_1\text{-}C_6)$alkoxy,
$(C_2\text{-}C_6)$alkenyl,
$NH_2$,
$NH(C_1\text{-}C_6)$alkyl, or
$N((C_1\text{-}C_6)$alkyl$)_2$.

The invention is also directed to a compound which is

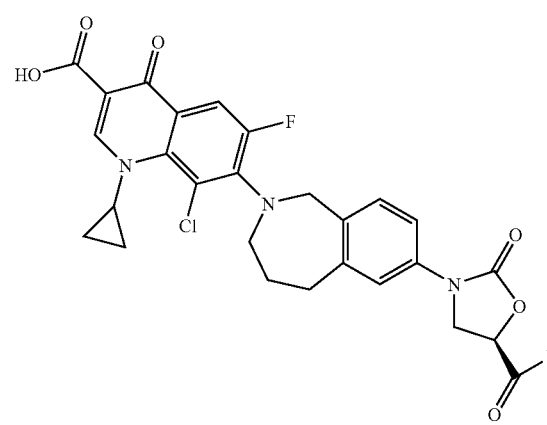

7-[7-(5-Carbamoyl-2-oxo-oxazolidin-3-yl)-1,3,4,5-tetrahydro-benzo[c]azepin-2-yl]-8-chloro-1-cyclopropyl-6-fluoro-4-oxo-1,4-dihydro-quinoline-3-carboxylic acid;

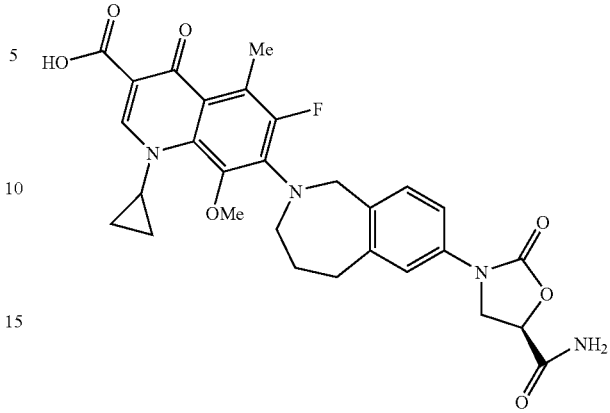

7-[7-(5-Carbamoyl-2-oxo-oxazolidin-3-yl)-1,3,4,5-tetrahydro-benzo[c]azepin-2-yl]-1-cyclopropyl-6-fluoro-8-methoxy-5-methyl-4-oxo-1,4-dihydro-quinoline-3-carboxylic acid;

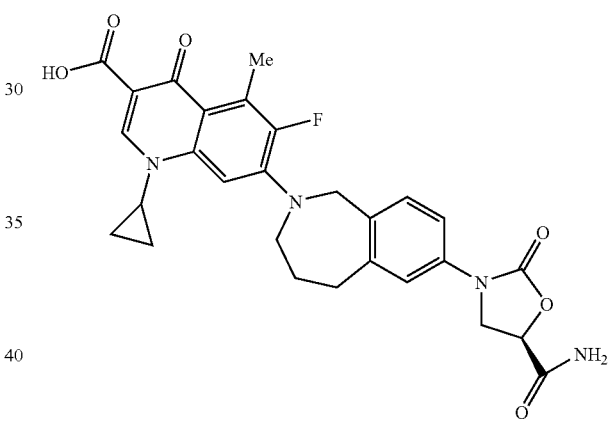

7-[7-(5-Carbamoyl-2-oxo-oxazolidin-3-yl)-1,3,4,5-tetrahydro-benzo[c]azepin-2-yl]-1-cyclopropyl-6-fluoro-5-methyl-4-oxo-1,4-dihydro-quinoline-3-carboxylic acid;

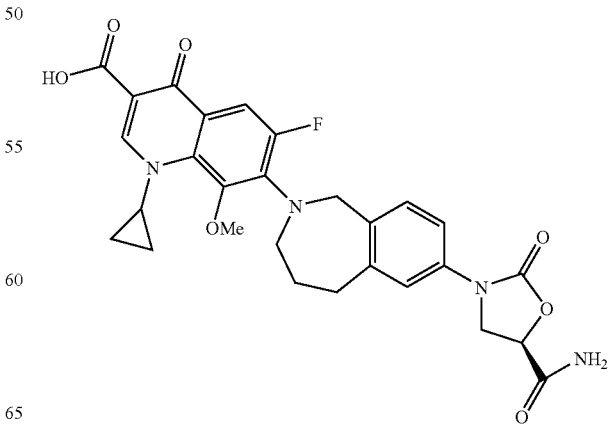

7-[7-(5-Carbamoyl-2-oxo-oxazolidin-3-yl)-1,3,4,5-tetrahydro-benzo[c]azepin-2-yl]-1-cyclopropyl-6-fluoro-8-methoxy-4-oxo-1,4-dihydro-quinoline-3-carboxylic acid;

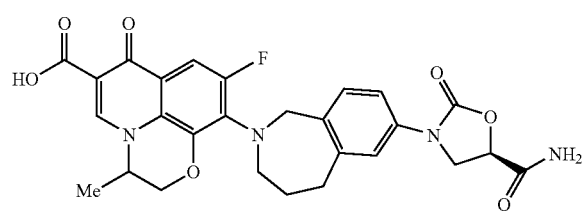

9-[7-(5-Carbamoyl-2-oxo-oxazolidin-3-yl)-1,3,4,5-tetrahydro-benzo[c]azepin-2-yl]-8-fluoro-3-methyl-6-oxo-2,3-dihydro-6H-1-oxa-3a-aza-phenalene-5-carboxylic acid;

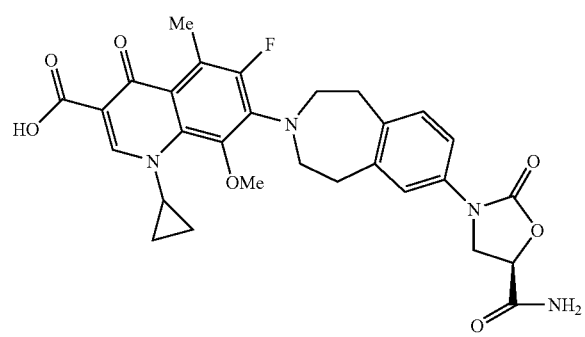

7-[7-(5-Carbamoyl-2-oxo-oxazolidin-3-yl)-1,2,4,5-tetrahydro-benzo[d]azepin-3-yl]-1-cyclopropyl-6-fluoro-8-methoxy-5-methyl 4-oxo-1,4-dihydro-quinoline-3-carboxylic acid;

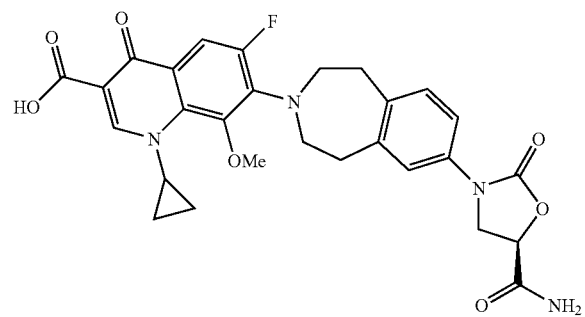

7-[7-(5-Carbamoyl-2-oxo-oxazolidin-3-yl)-1,2,4,5-tetrahydro-benzo[d]azepin-3-yl]-1-cyclopropyl-6-fluoro-8-methoxy-4-oxo-1,4-dihydro-quinoline-3-carboxylic acid;

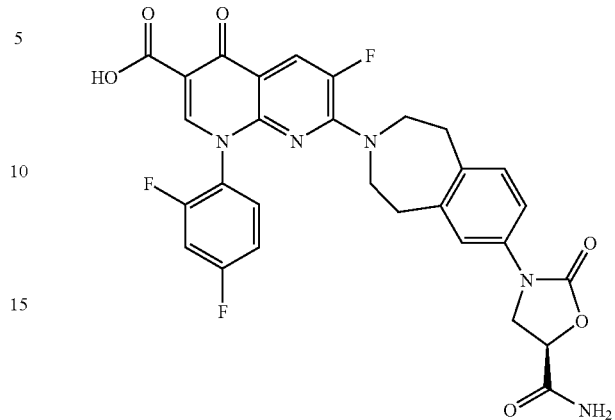

7-[7-(5-Carbamoyl-2-oxo-oxazolidin-3-yl)-1,2,4,5-tetrahydro-benzo[d]azepin-3-yl]-1-(2,4-difluoro-phenyl)-6-fluoro-4-oxo-1,4-dihydro-[1,8]naphthyridine-3-carboxylic acid;

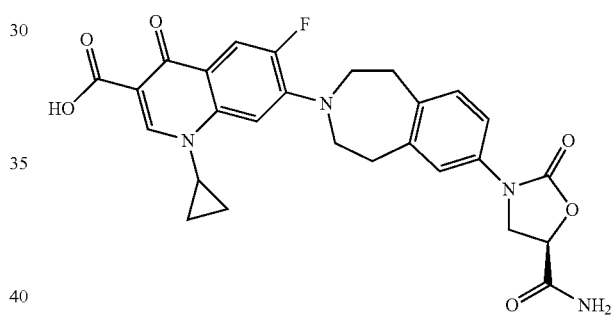

7-[7-(5-Carbamoyl-2-oxo-oxazolidin-3-yl)-1,2,4,5-tetrahydro-benzo[d]azepin-3-yl]-1-cyclopropyl-6-fluoro-4-oxo-1,4-dihydro-quinoline-3-carboxylic acid;

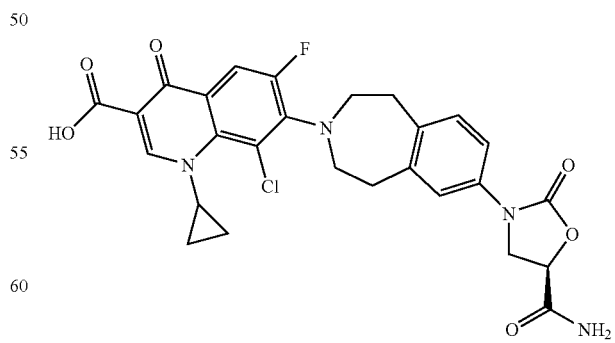

7-[7-(5-Carbamoyl-2-oxo-oxazolidin-3-yl)-1,2,4,5-tetrahydro-benzo[d]azepin-3-yl]-8-chloro-1-cyclopropyl-6-fluoro-4-oxo-1,4-dihydro-quinoline-3-carboxylic acid;

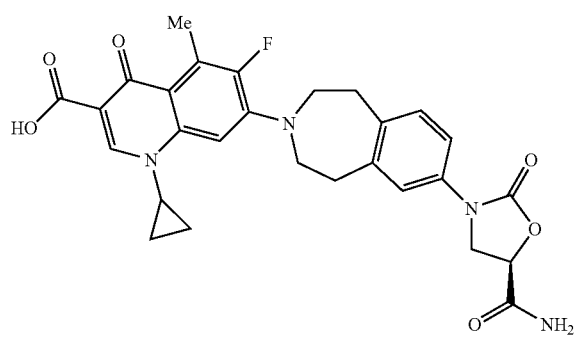

7-[7-(5-Carbamoyl-2-oxo-oxazolidin-3-yl)-1,2,4,5-tetrahydro-benzo[d]azepin-3-yl]-1-cyclopropyl-6-fluoro-5-methyl-4-oxo-1,4-dihydro-quinoline-3-carboxylic acid;

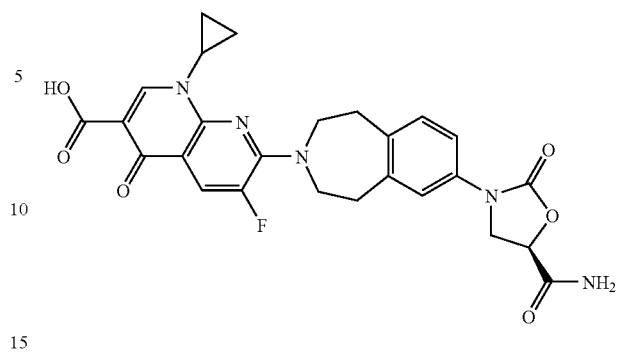

7-[7-(5-Carbamoyl-2-oxo-oxazolidin-3-yl)-1,2,4,5-tetrahydro-benzo[d]azepin-3-yl]-1-cyclopropyl-6-fluoro-4-oxo-1,4-dihydro-[1,8]naphthyridine-3-carboxylic acid;

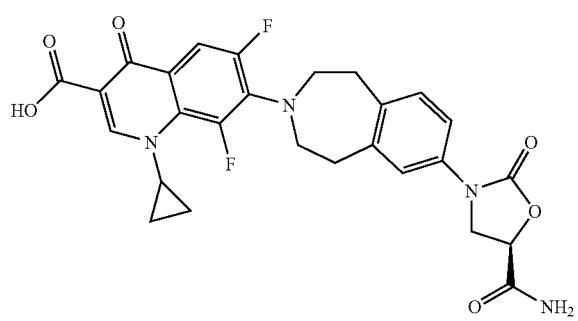

7-[7-(5-Carbamoyl-2-oxo-oxazolidin-3-yl)-1,2,4,5-tetrahydro-benzo[d]azepin-3-yl]-1-cyclopropyl-6,8-difluoro-4-oxo-1,4-dihydro-quinoline-3-carboxylic acid;

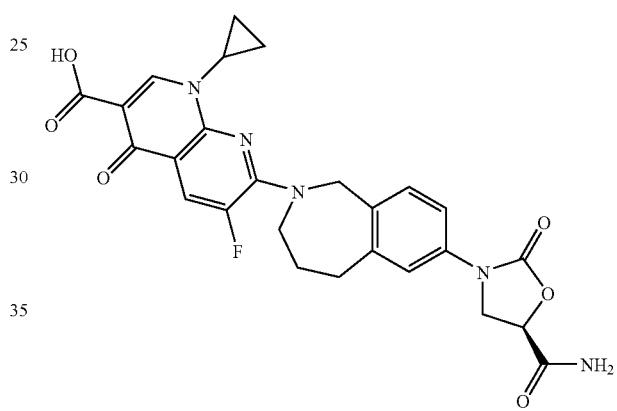

7-[7-(5-Carbamoyl-2-oxo-oxazolidin-3-yl)-1,3,4,5-tetrahydro-benzo[c]azepin-2-yl]-1-cyclopropyl-6-fluoro-4-oxo-1,4-dihydro-[1,8]naphthyridine-3-carboxylic acid;

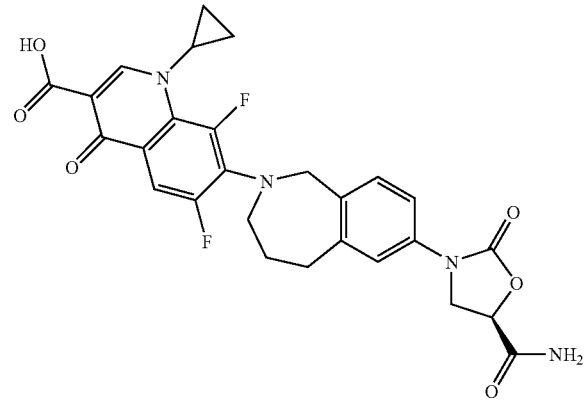

7-[7-(5-Carbamoyl-2-oxo-oxazolidin-3-yl)-1,3,4,5-tetrahydro-benzo[c]azepin-2-yl]-1-cyclopropyl-6,8-difluoro-4-oxo-1,4-dihydro-quinoline-3-carboxylic acid;

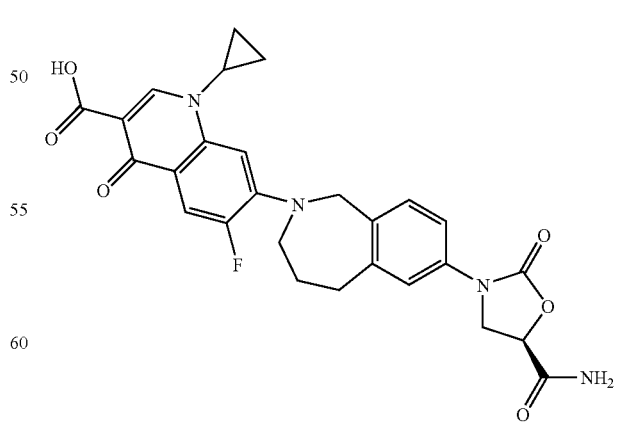

7-[7-(5-Carbamoyl-2-oxo-oxazolidin-3-yl)-1,3,4,5-tetrahydro-benzo[c]azepin-2-yl]-1-cyclopropyl-6-fluoro-4-oxo-1,4-dihydro-quinoline-3-carboxylic acid;

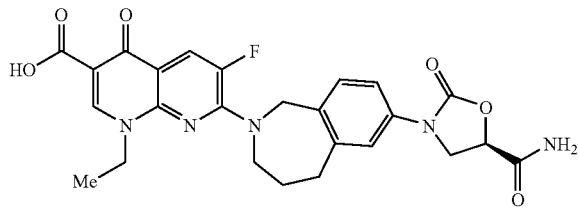

7-[7-(5-Carbamoyl-2-oxo-oxazolidin-3-yl)-1,3,4,5-tetrahydro-benzo[c]azepin-2-yl]-1-ethyl-6-fluoro-4-oxo-1,4-dihydro-[1,8]naphthyridine-3-carboxylic acid; or

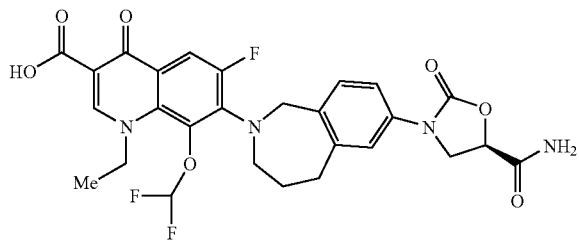

7-[7-(5-Carbamoyl-2-oxo-oxazolidin-3-yl)-1,3,4,5-tetrahydro-benzo[c]azepin-2-yl]-8-difluoromethoxy-1-ethyl-6-fluoro-4-oxo-1,4-dihydro-quinoline-3-carboxylic acid.

The invention is further directed to a compound of formula III

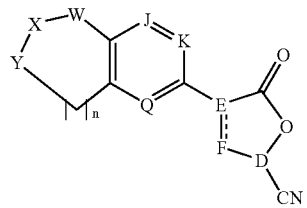

III or a pharmaceutically acceptable salt thereof wherein
either D is N, E is C, and F is CH when "..." is a bond,
  or D is CH, E is N, and F is $CH_2$ when "..." is absent;
J, K, Q independently are $CR_b$ or N, with the proviso that when any one of J, K, or Q is N, then the other two are $CR_b$;
"..." are each independently absent; or are bonds;
$R_b$ is H;
  halo,
  $(C_1-C_8)$alkyl,
  $(C_3-C_6)$cycloalkyl,
  O—$(C_1-C_4)$alkyl,
  O—$(C_3-C_6)$cycloalkyl,
  S—$(C_1-C_4)$alkyl,
  S—$(C_3-C_6)$cycloalkyl,
  $NH_2$,
  $NH(C_1-C_4)$alkyl,
  $N((C_1-C_4)$alkyl$)_2$, or
  NH—$(C_3-C_6)$cycloalkyl;
n is 0, 1, or 2;
at least one of W, X, or Y is NP and the other two are each independently absent, —$CH_2$—,
—$CH_2$—$CH_2$—, or
—C≡C—;
P is

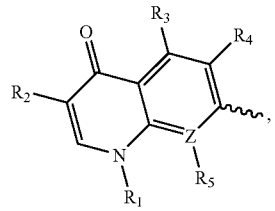

wherein

" $\sim\sim\sim$ "

indicates the point of attachment,
  Z is N or C, provided that when Z is N, $R_5$ is absent at that position;
  $R_1$ is $(C_1-C_6)$alkyl,
    halo$(C_1-C_6)$alkyl,
    $(C_3-C_6)$cycloalkyl,
    halo$(C_3-C_6)$cycloalkyl,
    aryl, and
    heteroaryl;
  $R_2$ is OH,
    $O(C_1-C_6)$alkyl,
    $O(C_3-C_6)$cycloalkyl,

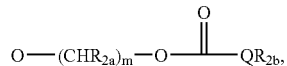

wherein m is an integer of from 1 to 10, Q is O or is absent, and $R_{2a}$ is H or $(C_1-C_6)$alkyl and $R_{2b}$ is $(C_1-C_6)$alkyl, aryl, or heteroaryl,
  O—$(CHR_{2a})_n$—Y, wherein $R_{2a}$ is as defined above, n is an integer of from 2 to 10, Y is OH or $NR_{2c}R_{2d}$, wherein $R_{2c}$ and $R_{2d}$ are each independently H, $(C_1-C_6)$alkyl, or $(C_3-C_6)$cycloalkyl, or
  $NR_{2d}$, wherein $R_{2d}$ is as defined above,

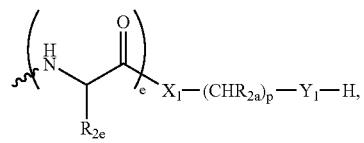

wherein

"⌇⌇⌇⌇"

indicates the point of attachment, 2a is as defined above, $R_{2e}$ is H or $(C_1-C_6)$alkyl, e is an integer of from 1 to 10, p is an integer of from 2 to 10, and $X_1$ and $Y_2$ are each independently NH or O;

$R_3$, $R_4$, and $R_5$ are each independently H,
halo,
$NH_2$,
$(C_1-C_6)$alkyl,
halo$(C_1-C_6)$alkyl,
$(C_1-C_6)$alkoxy, or
halo$(C_1-C_6)$alkoxy; or $R_1$ and $R_5$, together with the carbons to which they are attached, are joined to form a 6-membered substituted or unsubstituted ring containing 1 or 2 heteroatroms selected from NH, N$(C_1-C_6)$alkyl, or O; and $R_6$ is H,
OH,
$(C_1-C_6)$alkyl,
$(C_3-C_6)$cycloalkyl,
$(C_1-C_6)$alkoxy,
$(C_2-C_6)$alkenyl,
$NH_2$,
NH$(C_1-C_6)$alkyl, or
N$((C_1-C_6)$alkyl$)_2$.

What is also provided is a compound which is

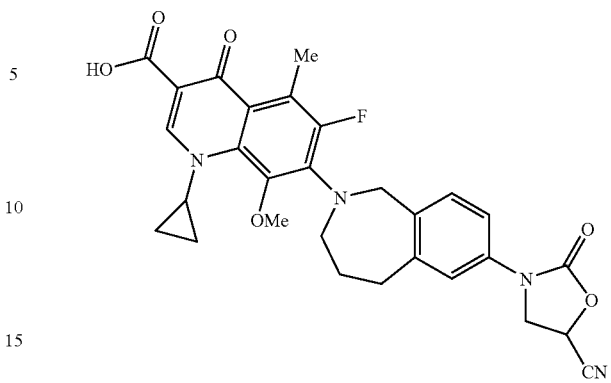

7-[7-(5-Cyano-2-oxo-oxazolidin-3-yl)-1,3,4,5-tetrahydro-benzo[c]azepin-2-yl]-1-cyclopropyl-6-fluoro-8-methoxy-5-methyl-4-oxo-1,4-dihydro-quinoline-3-carboxylic acid;

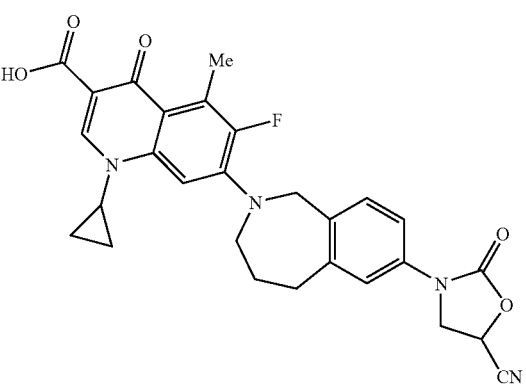

7-[7-(5-Cyano-2-oxo-oxazolidin-3-yl)-1,3,4,5-tetrahydro-benzo[c]azepin-2-yl]-1-cyclopropyl-6-fluoro-5-methyl-4-oxo-1,4-dihydro-quinoline-3-carboxylic acid;

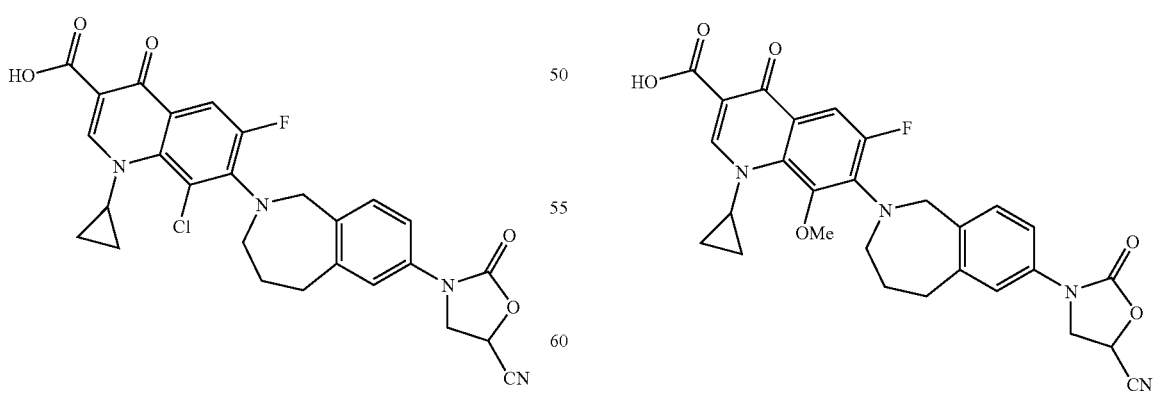

8-Chloro-7-[7-(5-cyano-2-oxo-oxazolidin-3-yl)-1,3,4,5-tetrahydro-benzo[c]azepin-2-yl]-1-cyclopropyl-6-fluoro-4-oxo-1,4-dihydro-quinoline-3-carboxylic acid;

7-[7-(5-Cyano-2-oxo-oxazolidin-3-yl)-1,3,4,5-tetrahydro-benzo[c]azepin-2-yl]-1-cyclopropyl-6-fluoro-8-methoxy-4-oxo-1,4-dihydro-quinoline-3-carboxylic acid;

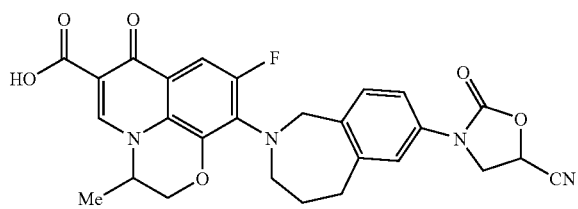

9-[7-(5-Cyano-2-oxo-oxazolidin-3-yl)-1,3,4,5-tetrahydro-benzo[c]azepin-2-yl]-8-fluoro-3-methyl-6-oxo-2,3-dihydro-6H-1-oxa-3a-aza-phenalene-5-carboxylic acid;

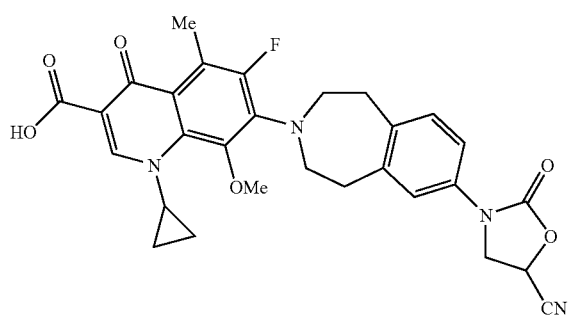

7-[7-(5-Cyano-2-oxo-oxazolidin-3-yl)-1,2,4,5-tetrahydro-benzo[d]azepin-3-yl]-1-cyclopropyl-6-fluoro-8-methoxy-5-methyl-4-oxo-1,4-dihydro-quinoline-3-carboxylic acid;

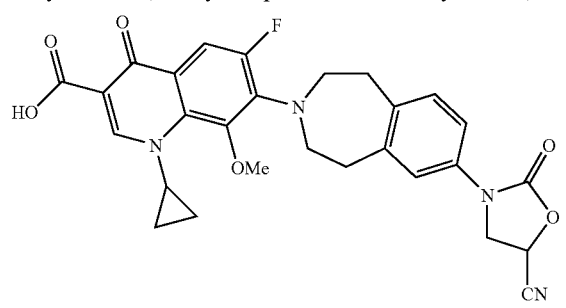

7-[7-(5-Cyano-2-oxo-oxazolidin-3-yl)-1,2,4,5-tetrahydro-benzo[d]azepin-3-yl]-1-cyclopropyl-6-fluoro-8-methoxy-4-oxo-1,4-dihydro-quinoline-3-carboxylic acid;

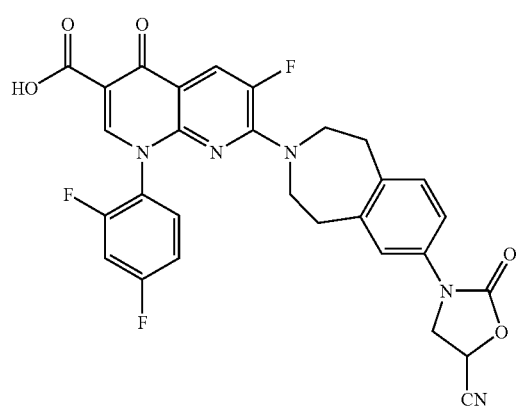

7-[7-(5-Cyano-2-oxo-oxazolidin-3-yl)-1,2,4,5-tetrahydro-benzo[d]azepin-3-yl]-1-(2,4-difluoro-phenyl)-6-fluoro-4-oxo-1,4-dihydro-[1,8]naphthyridine-3-carboxylic acid;

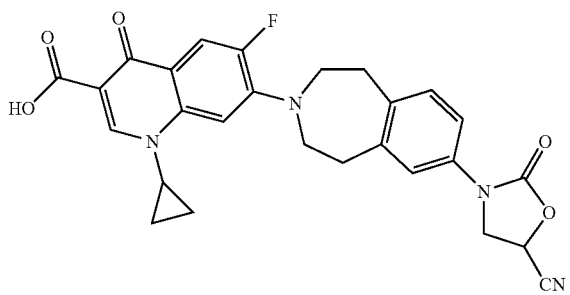

7-[7-(5-Cyano-2-oxo-oxazolidin-3-yl)-1,2,4,5-tetrahydro-benzo[d]azepin-3-yl]-1-cyclopropyl-6-fluoro-4-oxo-1,4-dihydro-quinoline-3-carboxylic acid;

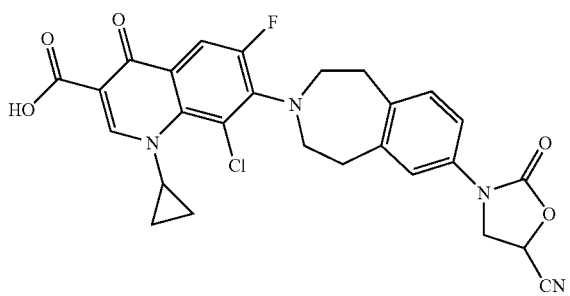

8-Chloro-7-[7-(5-cyano-2-oxo-oxazolidin-3-yl)-1,2,4,5-tetrahydro-benzo[d]azepin-3-yl]-1-cyclopropyl-6-fluoro-4-oxo-1,4-dihydro-quinoline-3-carboxylic acid;

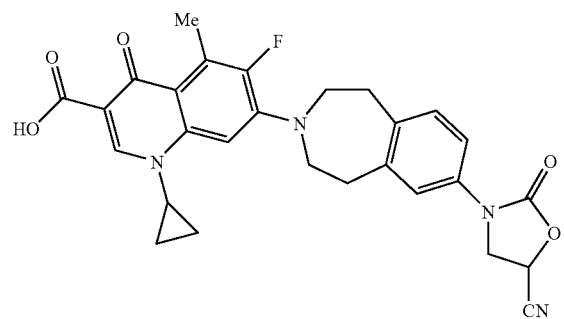

7-[7-(5-Cyano-2-oxo-oxazolidin-3-yl)-1,2,4,5-tetrahydro-benzo[d]azepin-3-yl]-1-cyclopropyl-6-fluoro-5-methyl-4-oxo-1,4-dihydro-quinoline-3-carboxylic acid;

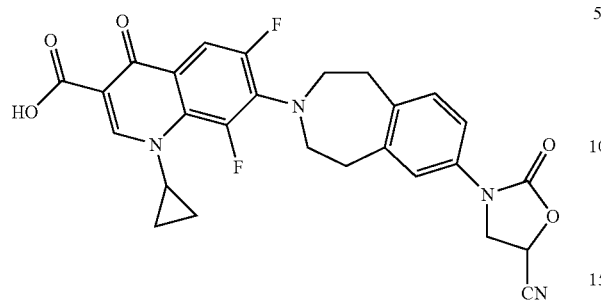

7-[7-(5-Cyano-2-oxo-oxazolidin-3-yl)-1,2,4,5-tetrahydro-benzo[d]azepin-3-yl]-1-cyclopropyl-6,8-difluoro-4-oxo-1,4-dihydro-quinoline-3-carboxylic acid;

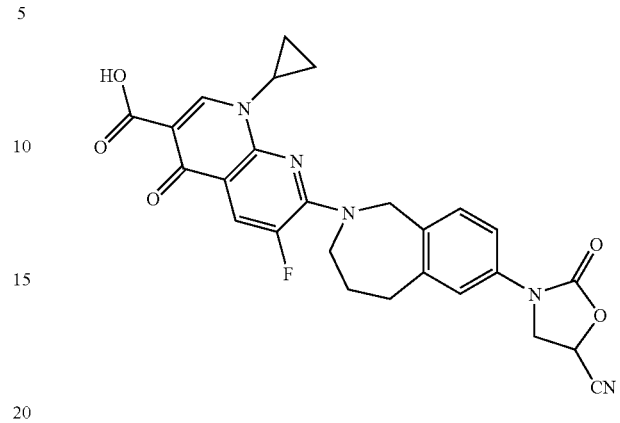

7-[7-(5-Cyano-2-oxo-oxazolidin-3-yl)-1,3,4,5-tetrahydro-benzo[c]azepin-2-yl]-1-cyclopropyl-6-fluoro-4-oxo-1,4-dihydro-[1,8]naphthyridine-3-carboxylic acid;

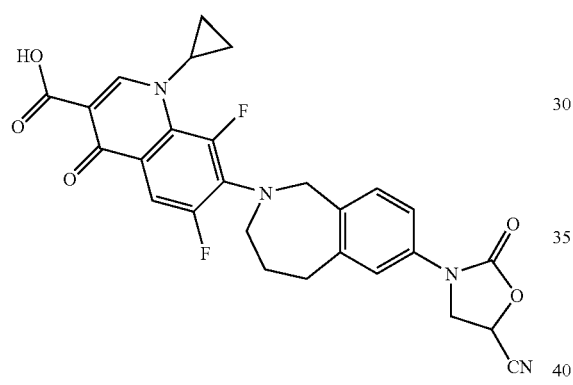

7-[7-(5-Cyano-2-oxo-oxazolidin-3-yl)-1,3,4,5-tetrahydro-benzo[c]azepin-2-yl]-1-cyclopropyl-6,8-difluoro-4-oxo-1,4-dihydro-quinoline-3-carboxylic acid;

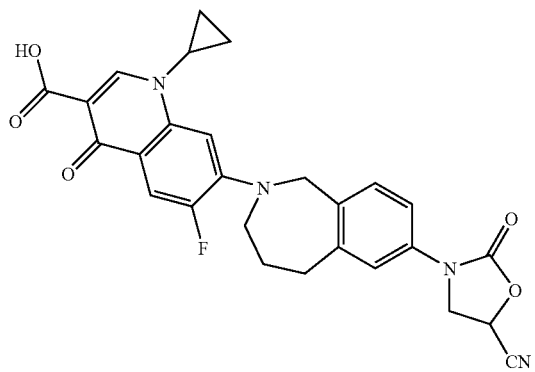

7-[7-(5-Cyano-2-oxo-oxazolidin-3-yl)-1,3,4,5-tetrahydro-benzo[c]azepin-2-yl]-1-cyclopropyl-6-fluoro-4-oxo-1,4-dihydro-quinoline-3-carboxylic acid;

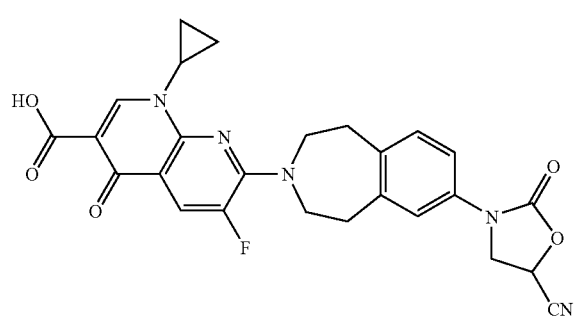

7-[7-(5-Cyano-2-oxo-oxazolidin-3-yl)-1,2,4,5-tetrahydro-benzo[d]azepin-3-yl]-1-cyclopropyl-6-fluoro-4-oxo-1,4-dihydro-[1,8]naphthyridine-3-carboxylic acid;

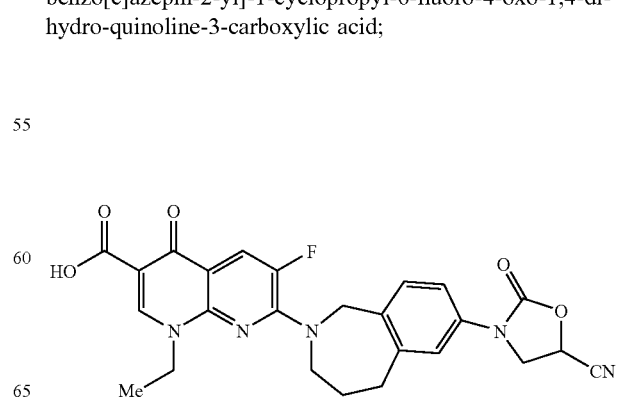

7-[7-(5-Cyano-2-oxo-oxazolidin-3-yl)-1,3,4,5-tetrahydro-benzo[c]azepin-2-yl]-1-ethyl-6-fluoro-4-oxo-1,4-dihydro-[1,8]naphthyridine-3-carboxylic acid; or

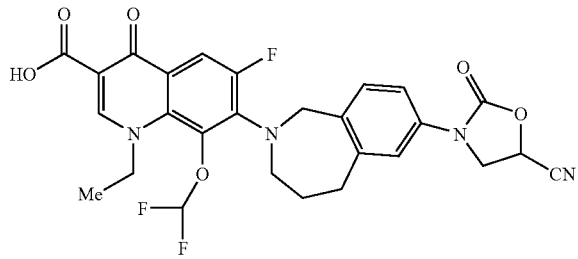

7-[7-(5-Cyano-2-oxo-oxazolidin-3-yl)-1,3,4,5-tetrahydro-benzo[c]azepin-2-yl]-8-difluoromethoxy-1-ethyl-6-fluoro-4-oxo-1,4-dihydro-quinoline-3-carboxylic acid.

The invention also provides a compound of A compound of formula IV

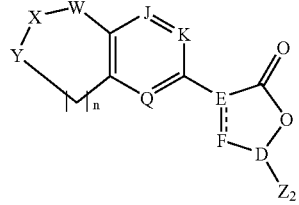

or a pharmaceutically acceptable salt thereof wherein $Z_2$ is

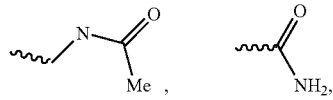

or CN;

either D is N, E is C, and F is CH when "..." is a bond, or D is CH, E is N, and F is CH$_2$ when "..." is absent;

J, K, Q independently are CR$_b$ or N, with the proviso that when any one of J, K, or Q is N, then the other two are CR$_b$;

"..." are each independently absent; or are bonds;

R$_a$ is H,
(C$_1$-C$_8$)alkyl,
(C$_3$-C$_6$)cycloalkyl,
O—(C$_1$-C$_4$)alkyl,
O—(C$_3$-C$_6$)cycloalkyl,
S—(C$_1$-C$_4$)alkyl,
S—(C$_3$-C$_6$)cycloalkyl,
NH$_2$,
NH(C$_1$-C$_4$)alkyl,
N((C$_1$-C$_4$)alkyl)$_2$, or
NH—(C$_3$-C$_6$)cycloalkyl, R$_b$ is H;
halo,
(C$_1$-C$_8$)alkyl,
(C$_3$-C$_6$)cycloalkyl,
O—(C$_1$-C$_4$)alkyl,
O—(C$_3$-C$_6$)cycloalkyl,
S—(C$_1$-C$_4$)alkyl,
S—(C$_3$-C$_6$)cycloalkyl,
NH$_2$,
NH(C$_1$-C$_4$)alkyl,
N((C$_1$-C$_4$)alkyl)$_2$, or
NH—(C$_3$-C$_6$)cycloalkyl;

n is 0, 1, or 2;

at least one of W, X, or Y is NP and the other two are each independently absent,
—CH$_2$—,
—CH$_2$—CH$_2$—, or
—C=C—;

P is

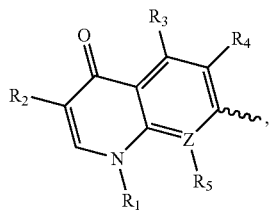

wherein

"~~~"

indicates the point of attachment,

Z is N or C, provided that when Z is N, R$_5$ is absent at that position;

R$_1$ is (C$_1$-C$_6$)alkyl,
halo(C$_1$-C$_6$)alkyl,
(C$_3$-C$_6$)cycloalkyl,
halo(C$_3$-C$_6$)cycloalkyl,
aryl, and
heteroaryl;

R$_2$ is OH,
O(C$_1$-C$_6$)alkyl,
O(C$_3$-C$_6$)cycloalkyl,

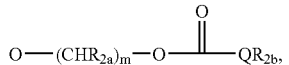

wherein m is an integer of from 1 to 10, Q is O or is absent, and R$_{2a}$ is H or (C$_1$-C$_6$)alkyl and R$_{2b}$ is (C$_1$-C$_6$)alkyl, aryl, or heteroaryl, O—(CHR$_{2a}$)$_n$—Y, wherein R$_{2a}$ is as defined above, n is an integer of from 2 to 10, Y is OH or NR$_{2c}$R$_{2d}$, wherein R$_{2c}$ and R$_{2d}$ are each independently H, (C$_1$-C$_6$)alkyl, or (C$_3$-C$_6$)cycloalkyl, or NR$_{2d}$, wherein R$_{2d}$ is as defined above,

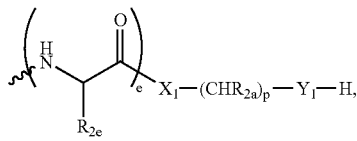

wherein

"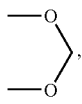"

indicates the point of attachment, 2a is as defined above, $R_{2e}$ is H or $(C_1-C_6)$alkyl, e is an integer of from 1 to 10, p is an integer of from 2 to 10, and $X_1$ and $Y_1$ are each independently NH or O;

$R_3$, $R_4$, and $R_5$ are each independently H,
halo,
$NH_2$,
$(C_1-C_6)$alkyl,
halo$(C_1-C_6)$alkyl,
$(C_1-C_6)$alkoxy, or
halo$(C_1-C_6)$alkoxy; or
$R_1$, and $R_5$, together with the carbons to which they are attached, are joined to form a 6-membered substituted or unsubstituted ring containing 1 or 2 heteroatroms selected from NH, $N(C_1-C_6)$alkyl, O.

The invention also provides a pharmaceutical formulation comprising a compound of formulas I, II, or III, admixed with a pharmaceutically acceptable diluent, carrier, or excipient.

The invention also provides a method of treating a bacterial infection in a mammal, comprising administering to a mammal in need thereof an effective amount of a compound of formulas I, II, or III.

DETAILED DESCRIPTION OF THE INVENTION

Reference will now be made in detail to presently preferred compositions or embodiments and methods of the invention, which constitute the best modes of practicing the invention presently known to the inventors.

The term "alkyl" as used herein refers to a straight or branched hydrocarbon of from 1 to 11 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents selected from lower alkoxy, lower thioalkoxy, halogen, nitro, cyano, oxo, thio, —OH, —SH, —F, —$CF_3$, —$OCF_3$, —$NO_2$, —$CO_2H$, —$CO_2C_1$-$C_6$alkyl, —$NH_2$, —$NHC_1$-$C_6$alkyl,

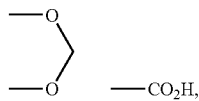

—$CONR^8R^9$, or —$N(C_1-C_6alkyl)_2$.

The terms "$(C_1-C_8)$alkyl", "$(C_1-C_6)$alkyl", and "$(C_1-C_4)$alkyl" as used herein refer to subsets of alkyl which mean a straight or branched hydrocarbon radical having from 1 to 8, 1 to 6, or 1 to 4 carbon atoms respectivly, and include, for example, methyl, ethyl, n-propyl, isopropyl, n-butyl, sec-butyl, isobutyl, tert-butyl, n-pentyl, n-hexyl, n-heptyl, and n-octyl and the like.

The term "$(C_3-C_6)$cycloalkyl" means a hydrocarbon ring containing from 3 to 6 carbon atoms, for example, cyclopropyl, cyclobutyl, cyclopentyl, or cyclohexyl. Where possible, the cycloalkyl group may contain double bonds, for example, 3-cyclohexen-1-yl. The cycloalkyl ring may be unsubstituted or substituted by one or more substituents selected from alkyl, alkoxy, thioalkoxy, hydroxy, thiol, nitro, halogen, amino, alkyl and dialkylamino, formyl, carboxyl, CN, —NH—CO—R, —CO—NHR, —$CO_2R$, —COR, wherein R is defined as above, aryl, heteroaryl, wherein alkyl, aryl, and heteroaryl are as defined herein, or as indicated above for alkyl, alkenyl, and alkynyl substitutents. Examples of substituted cycloalkyl groups include fluorocyclopropyl, 2-iodocyclobutyl, 2,3-dimethylcyclopentyl, 2,2-dimethoxycyclohexyl, and 3-phenylcyclopentyl.

The term "halo" includes chlorine, fluorine, bromine, and iodine.

The term "aryl" means a cyclic or polycyclic aromatic ring having from 5 to 12 carbon atoms, and being unsubstituted or substituted with one or more of the substituent groups recited above for alkyl groups including, halogen, nitro, cyano —OH, —SH, —F, —$CF_3$, —$OCF_3$, —$NO_2$,

—CO₂H,

—$CO_2C_1$—$C_6$alkyl, —$NH_2$, —$NHC_1$—$C_6$ alkyl, —$CONR^aR^b$, wherein $R^a$ and $R^b$ are H or $(C_1-C_6)$alkyl or $C_3-C_6)$ cycloalkyl, $SO_2$alkyl, —$SO_2NH_2$, or —$N(C_1-C_6alkyl)_2$. Examples include, but are not limited to phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl, 3-chloro-2-methylphenyl, 3-chloro 4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, thienyl, naphthyl, 4-thionaphthyl, tetralinyl, anthracinyl, phenanthrenyl, benzonaphthenyl, fluorenyl, 2-acetamidofluoren-9-yl, and 4'-bromobiphenyl.

The term "heteroaryl" means an aromatic cyclic or polycyclic ring system having from 1 to 4 heteroatoms selected from N, O, and S. Typical heteroaryl groups include 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl. The heteroaryl groups may be unsubstituted or substituted by 1 to 3 substituents selected from those described above for alkyl, alkenyl, and alkynyl, for example, cyanothienyl and formylpyrrolyl. Preferred aromatic fused heterocyclic rings of from 8 to 10 atoms include but are not limited to 2-, 3-, 4-, 5-, 6-, 7-, or 8-quinolinyl, 1-, 3-, 4-, 5-, 6-, 7-, or 8-isoquinolinyl-, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl. Heteroaryl also includes 2- and 3- aminomethylfuran, 2- and 3- aminomethylthiophene and the like.

The term "heterocyclic" means a monocyclic, fused, bridged, or spiro bicyclic heterocyclic ring systems. Monocyclic heterocyclic rings contain from about 3 to 12 ring atoms, with from 1 to 5 heteroatoms selected from N, O, and S, and preferably from 3 to 7 member atoms, in the ring. Bicyclic heterocyclics contain from about 5 to about 17 ring atoms, preferably from 5 to 12 ring atoms. Bicyclic heterocyclic rings may be fused, spiro, or bridged ring systems. Examples of heterocyclic groups include cyclic ethers (oxiranes) such as ethyleneoxide, tetrahydrofuran, dioxane, and substituted cyclic ethers, wherein the substituents are those described above for the alkyl and cycloalkyl groups. Typical substituted cyclic ethers include propyleneoxide, phenyloxirane (styrene oxide), cis-2-butene-oxide (2,3-dimethyloxirane), 3-chlorotetrahydrofuran, 2,6-dimethyl-1,4-dioxane, and the like. Heterocycles containing nitrogen are groups such as pyrrolidine, piperidine, piperazine, tetrahydrotriazine, tetrahydropyrazole, and substituted groups such as 3-aminopyrrolidine, 4-methylpiperazin-1-yl, and the like. Typical sulfur containing heterocycles include tetrahydrothiophene, dihydro-1,3-dithiol-2-yl, and hexahydrothiophen 4-yl and substituted groups such as aminomethyl thiophene. Other commonly employed heterocycles include dihydro-oxathiol-4-yl, dihydro-1H-isoindole, tetrahydro-oxazolyl, tetrahydro-oxadiazolyl, tetrahydrodioxazolyl, tetrahydrooxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO$_2$ groups are also included. Examples include the sulfoxide and sulfone forms of tetrahydrothiophene.

The term "heteroaryl" means an aromatic cyclic or fused polycyclic ring system having from 1 to 8 heteroatoms selected from N, O, and S. The heteroaryl groups or fused heteroaryl groups may be unsubstituted or substituted by 1 to 3 substituents selected from those described above for alkyl, alkenyl, and alkynyl, for example, cyanothienyl and formylpyrrolyl.

Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

Aromatic fused heteroaryl groups of from 8 to 20 atoms include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenananthridinyl, 1-, 2-, 3-, 4-, 5-, 6-, 7-, 8-, or 9-acridinyl, 1-, 2-, 4-, 5-, 6-, 7-, 8-,or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 5-4H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

When a bond is represented by a line such as ". . . " this is meant to represent that the bond may be absent or present provided that the resultant compound is stable and of satisfactory valency.

The term "patient" means all mammals, including humans. Other examples of patients include cows, dogs, cats, goats, sheep, pigs, and rabbits.

A "therapeutically effective amount" is an amount of a compound of the present invention that when administered to a patient, elicits the desired therapeutic outcome; i.e., inhibits bacterial infection.

It will be appreciated by those skilled in the art that compounds of the invention having one or more chiral centers may exist in and be isolated in optically active and racemic forms. Some compounds may exhibit polymorphism. It is to be understood that the present invention encompasses any racemic, optically-active, polymorphic, geometric, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine activity or cytotoxicity using the standard tests described herein, or using other similar tests which are well known in the art.

A "prodrug" is an inactive derivative of a drug molecule that requires a chemical or an enzymatic biotransformation in order to release the active parent drug in the body.

Specific and preferred values for compounds of Formulas I, II, and III are listed below for radicals, substituents, and ranges are for illustration purposes only, and they do not exclude other defined values or other values within defined ranges for the radicals and substituents.

Thus, turning now to a compound of formula I, a specific value for A is NH, as designated in formula IA.

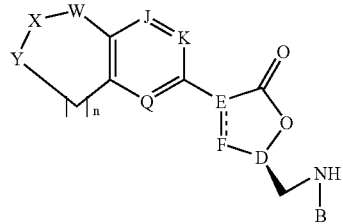

IA

A specific value for B is as designated in formula IB.

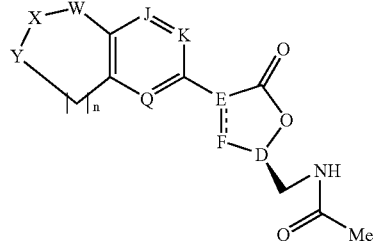

IB

Specific values for D, E, and F are as designated in formula IC.

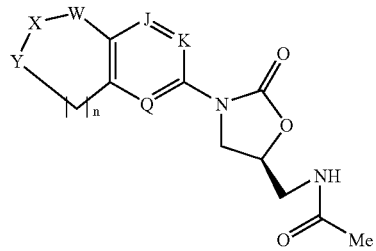

IC

A specific value for K is as designated in formula ID.

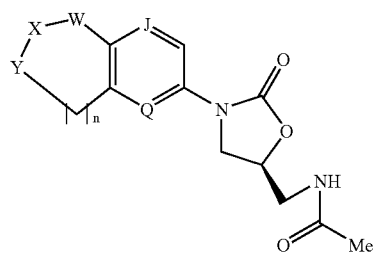

ID

A specific value for J is as designated in formula IE.

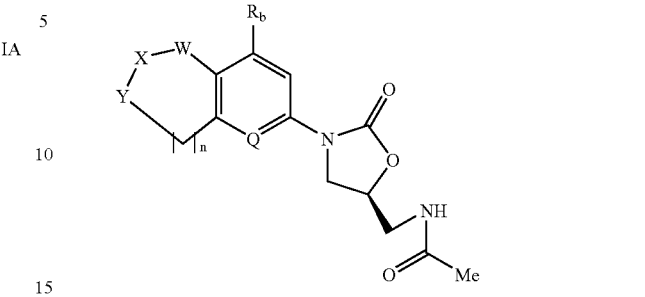

IE

A specific value for

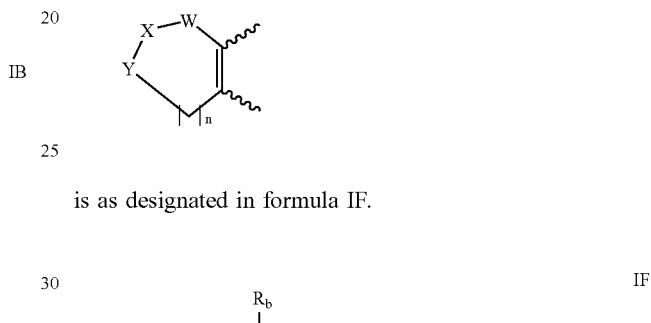

is as designated in formula IF.

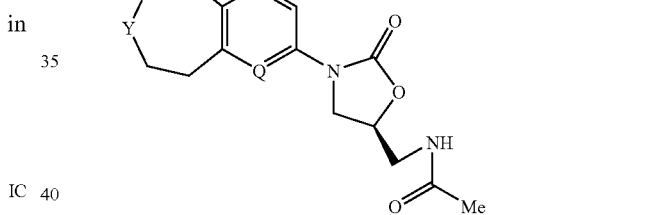

IF

Specific values for W, X, and Y are as designated in formulas IG-1, IG-2, and IG-3.

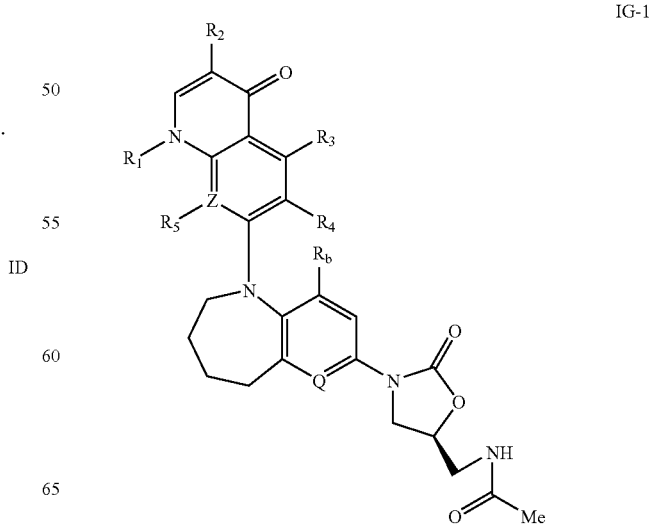

IG-1

-continued

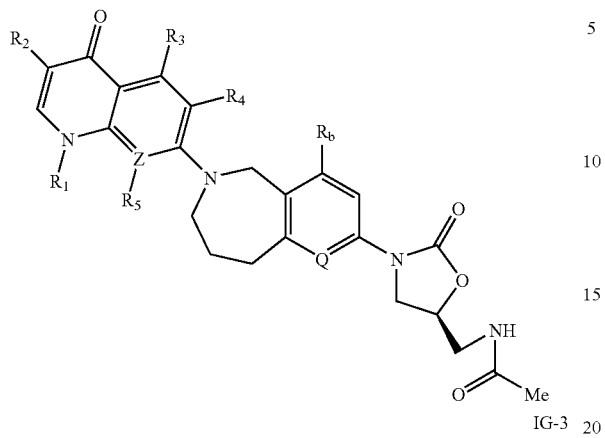
IG-2

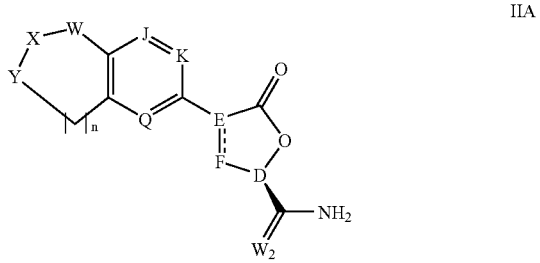
IIA

A specific value for $W_2$ is as designated in formula IIB.

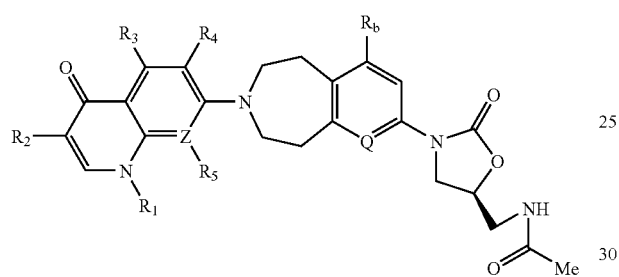
IG-3

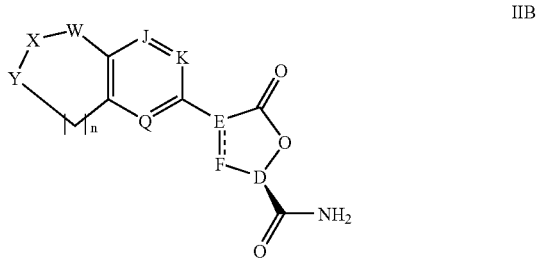
IIB

Specific values for $R_1$-$R_5$ in compounds of formula IG-1, IG-2, and IG-3 include:

$R_1$ is $(C_1$-$C_6)$alkyl, cyclopropanyl, fluorocyclopropanyl, phenyl, 1,3

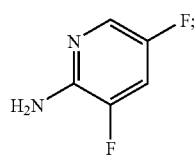

difluorophenyl, and $R_2$ is $CO_2H$;

$R_3$ is H, $NH_2$, or $(C_1$-$C_6)$alkyl;

$R_4$ is H or halo; and $R_5$ is H,
halo,
$NH_2$,
$(C_1$-$C_6)$alkyl,
halo$(C_1$-$C_6)$alkyl,
$(C_1$-$C_6)$alkoxy, or
halo$(C_1$-$C_6)$alkoxy; or $R_1$, and $R_5$, together with the carbons to which they are attached, are joined to form a 6-membered substituted or unsubstituted ring containing 1 heteroatom selected from NH, N$(C_1$-$C_6)$alkyl, or O.

Turning now to a compound of formula II, a specific value for $NR_6$ is as designated in formula IIA.

Specific values of D, E, and F are as designated in formula IIC.

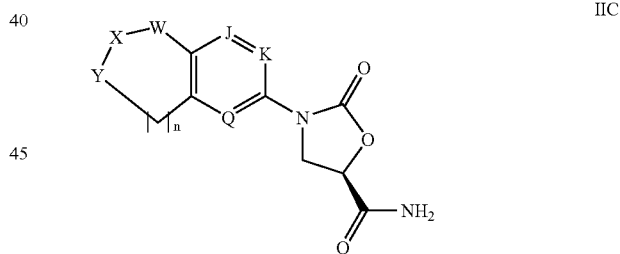
IIC

A specific value for K is as designated in formula IID.

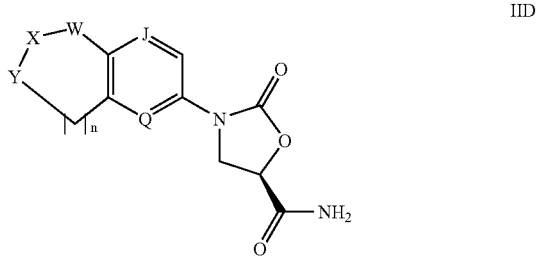
IID

A specific value of J is as designated in formula IIE.

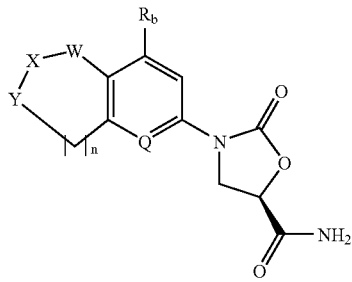

IIE

A specific value for

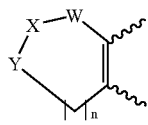

is as designated in formula IIF.

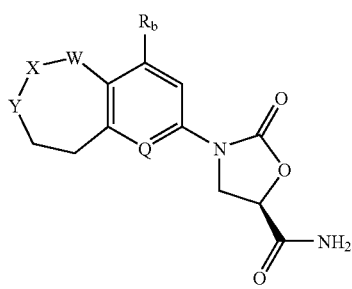

IIF

Specific values for W, X, and Y are as designated in formulas IIG-1, IIG-2, and IIG-3.

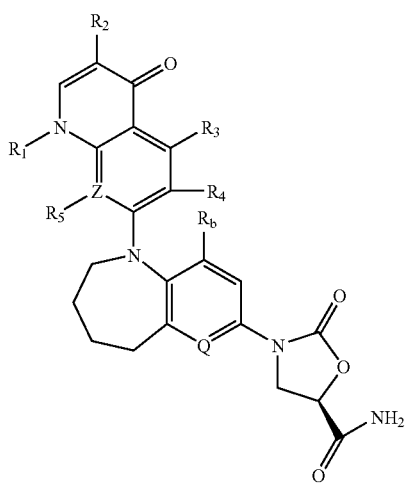

IIG-1

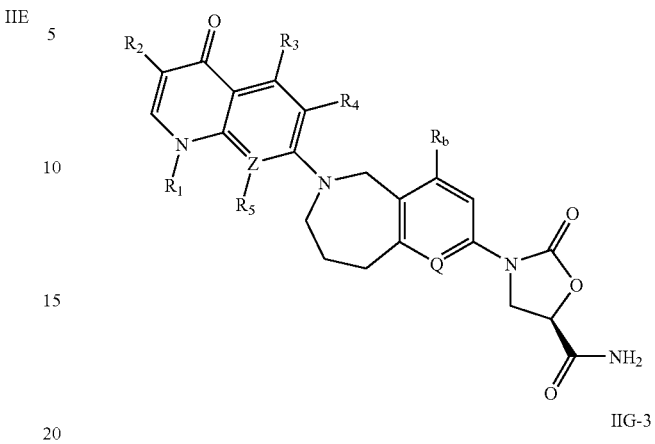

IIG-2

IIG-3

Specific values for $R_1$-$R_5$ in compounds of formula IIG-1, IIG-2, and IIG-3 include:

$R_1$ is $(C_1$-$C_6)$alkyl, cyclopropanyl, fluorocyclopropanyl, phenyl, 1,3

difluorophenyl, and $R_2$ is $CO_2H$;

$R_3$ is H, $NH_2$, or $(C_1$-$C_6)$alkyl;

$R_4$ is H or halo; and $R_5$ is H, halo, $NH_2$, $(C_1$-$C_6)$alkyl, halo$(C_1$-$C_6)$alkyl, $(C_1$-$C_6)$alkoxy, or halo$(C_1$-$C_6)$alkoxy; or $R_1$, and $R_5$, together with the carbons to which they are attached, are joined to form a 6-membered substituted or unsubstituted ring containing 1 heteroatom selected from NH, N$(C_1$-$C_6)$alkyl, or O.

Turning now to a compound of formula III, specific values for D, E, and F are aas designated in formula IIIA.

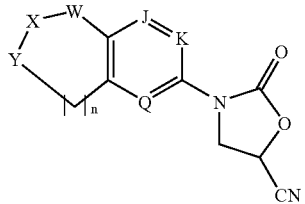

IIIA

A spcific value for K is as designated in formula IIIB.

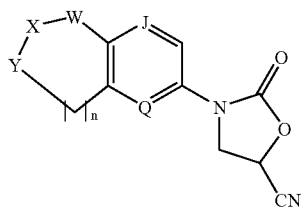

IIIB

A spcific value for J is as designated in formula IIIC.

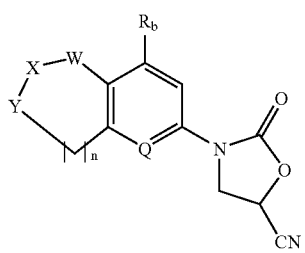

IIIC

A specific value for

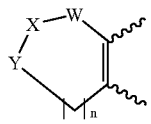

is as designated in formula IIID.

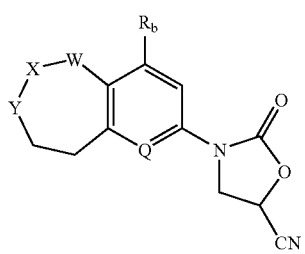

IIID

Specific values for W, X, and Y are as designated in formulas IIIE-1, IIIE-2, and IIIE-3.

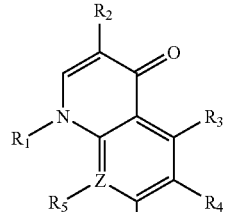

IIIE-1

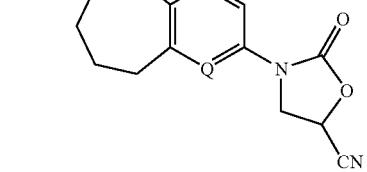

IIIE-2

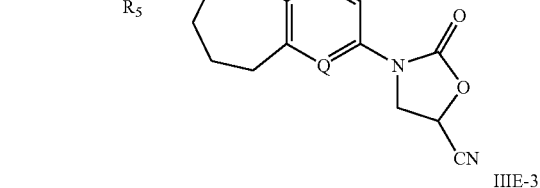

IIIE-3

Specific values for $R_1$-$R_5$ in compounds of formula IIIG-1, IIIG-2, and IIIG-3 include:

$R_1$ is $(C_1$-$C_6)$alkyl, cyclopropanyl, fluorocyclopropanyl, phenyl, 1,3

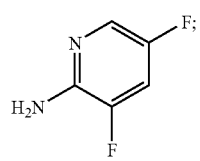

difluorophenyl, and $R_2$ is $CO_2H$;

$R_3$ is H, $NH_2$, or $(C_1$-$C_6)$alkyl;

$R_4$ is H or halo; and $R_5$ is H, halo,
NH$_2$,
(C$_1$-C$_6$)alkyl,
halo(C$_1$-C$_6$)alkyl,
(C$_1$-C$_6$)alkoxy, or
halo(C$_1$-C$_6$)alkoxy; or R$_1$, and R$_5$, together with the carbons to which they are attached, are joined to form a 6-membered substituted or unsubstituted ring containing 1 heteroatom selected from NH, N(C$_1$-C$_6$)alkyl, or O.

Preparation of Invention Compounds

As is readily apparent from this disclosure, compounds of the present invention are characterized by a quinone subunit which is covalently attached to a to a oxazolidinyl subunit. As retrosynthetically depicted in Scheme I, invention compounds can be prepared by coupling an appropriately substituted quinone subunit to an azepine-bearing oxazolidinone core. Reflecting the synthetic strategies summarized in Scheme I, the following section describing the preparation of the invention compounds has two sections. The first section summarizes the the preparation of oxazolidinone subunits. As a note, the preparation of the requisite oxazolidinone subunits was originally described in U.S. Provisional Patent Application Ser. No. 60/445,957, filed Feb. 7, 2003. The second section summarizes the coupling of quinone intermediates to the oxazolidinone subunits.

A. Preparation of Oxazolidinone Subunits

As retrosynthetically depicted in Scheme II, the oxazolidinone subunits used to prepare the invention compounds can be prepared from the corresponding benzocycloheptane via coupling procedures (D) available to the skilled artisan employing the oxazolidinone subunit itself or a synthon thereof. The requisite benzocycloheptyl compounds can be accessed via (A) annelation; (B) elaboration of a commercially available benzocycloheptane (B); or (C) ring expansion of a substituted di- tetrahydro naphthalene.

Scheme I

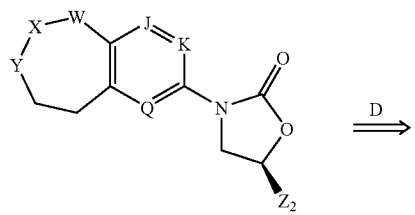

Scheme I

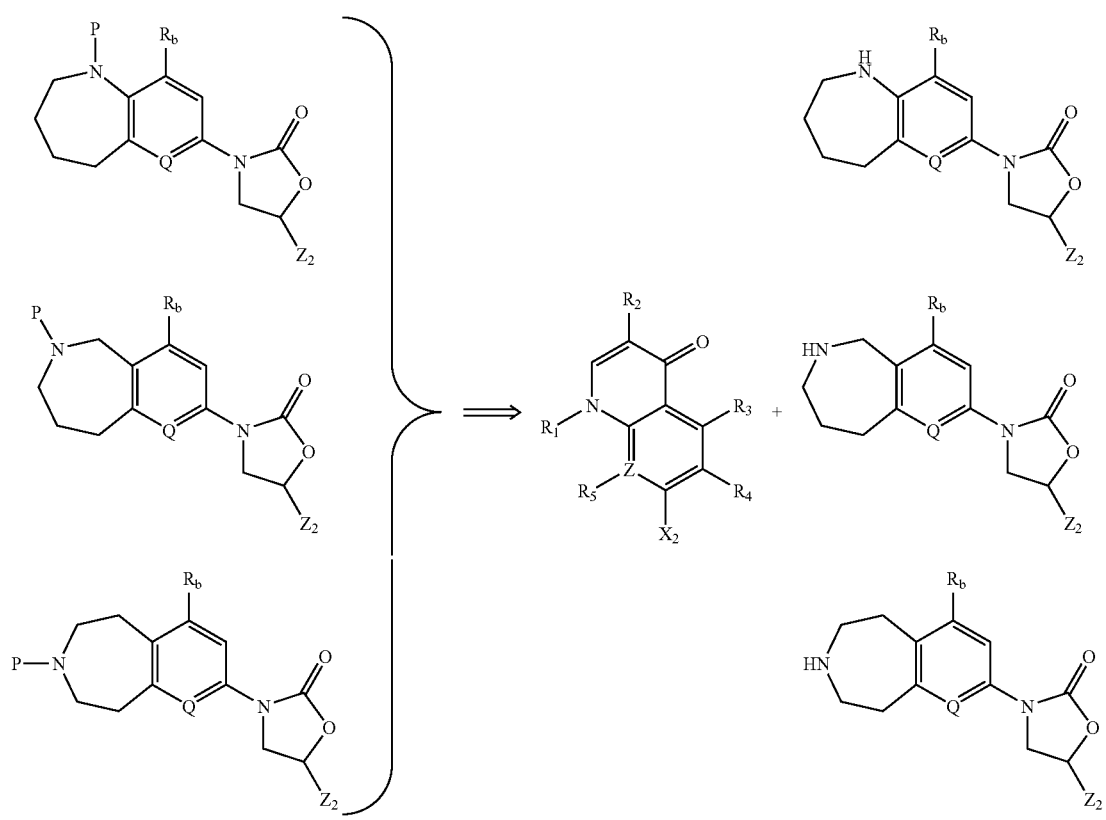

(R)-5-Hydroxymethyl-oxazolidin-2-one

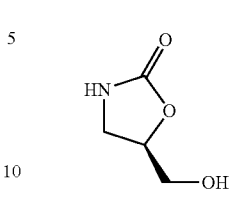

The title compound was prepared according to the procedure described by K. Danielmeier and E. Steckhan in Tetrahedron Assymetry 1995, 6(5), 1181-1190.

N-(2,4-Dimethoxy-benzyl)-N-(2-oxo-oxazolidin-5-ylmethyl)-acetamide

The title compound was prepared as described in Tetrahedron Letters, 2001, 42, 3681.

(S)-N-Oxiranylmethyl-acetamide

To a solution of (S)-N-acetyl-3-bromo-2-acetoxypropylamine (5 g, 0.021 mmol) in acetonitrile (20 mL) and methanol (20 mL) was added potassium carbonate (0.021 mmol) portion-wise. The reaction mixture was stirred at 0° C. for 1 hour and then warmed to room temperature slowly and stirred overnight. To it 50 mL of ethyl acetate was added and the precipitate was removed by filtration. Organic solvents were removed and the residue was dissolved in 60 mL of ethyl acetate and remaining precipitate was filtered and organic solution was concentration under reduced pressure to yield 1.6 g (90% yield) to obtain the title compound.

b. Preparation of Bicyclo-containing Oxazolidinones

Schemes 1 and 2 provide approaches to bicyclo subunits containing an N linkage at the 1-position. Hofmann-type ring enlargement of from chroman-4-one analogue 1-1A (step I) provides amide 1-2A. Nitration (step II), and sequential reduction of the amide (step III), and nitro moieties (step IV) affords amine 1-5A. Protection of the amine moieties in 1-5A (step V), followed by coupling to the oxazolidinone core following the chemistry described above for Scheme I (step VI) provides the intermediate 1-6A. The acetamide side chain of the oxazolidinone is then elaborated in steps VII-X, via mesylation (step VII), conversion to the azide (step VIII), reduction to the amine (step IX), acetamide formation (step X), and deprotection (step XI) to provide the target compound 1-12A.

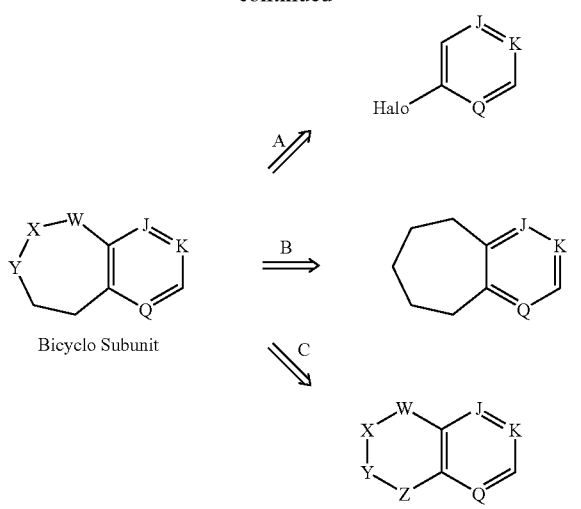

Bicyclo Subunit

1. Subunits wherein $Z_2$ is

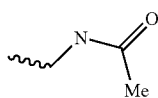

a. Preparation of Common Intermediates

The following compounds which were used in the synthesis of the compounds of the invention wherein $Z_2$ is

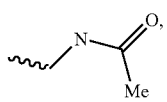

were prepared as follows.

Scheme 1

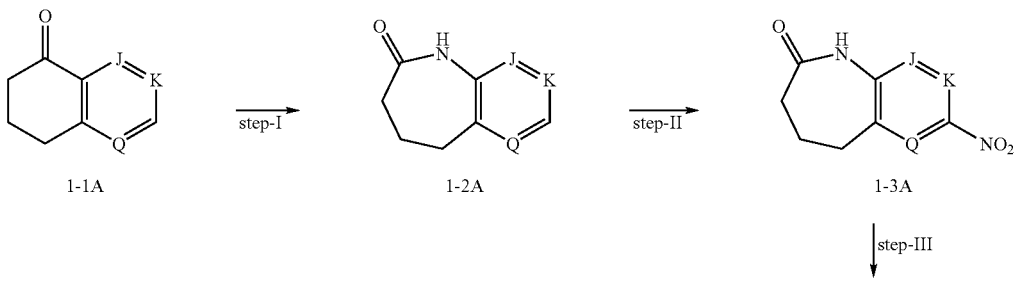

-continued
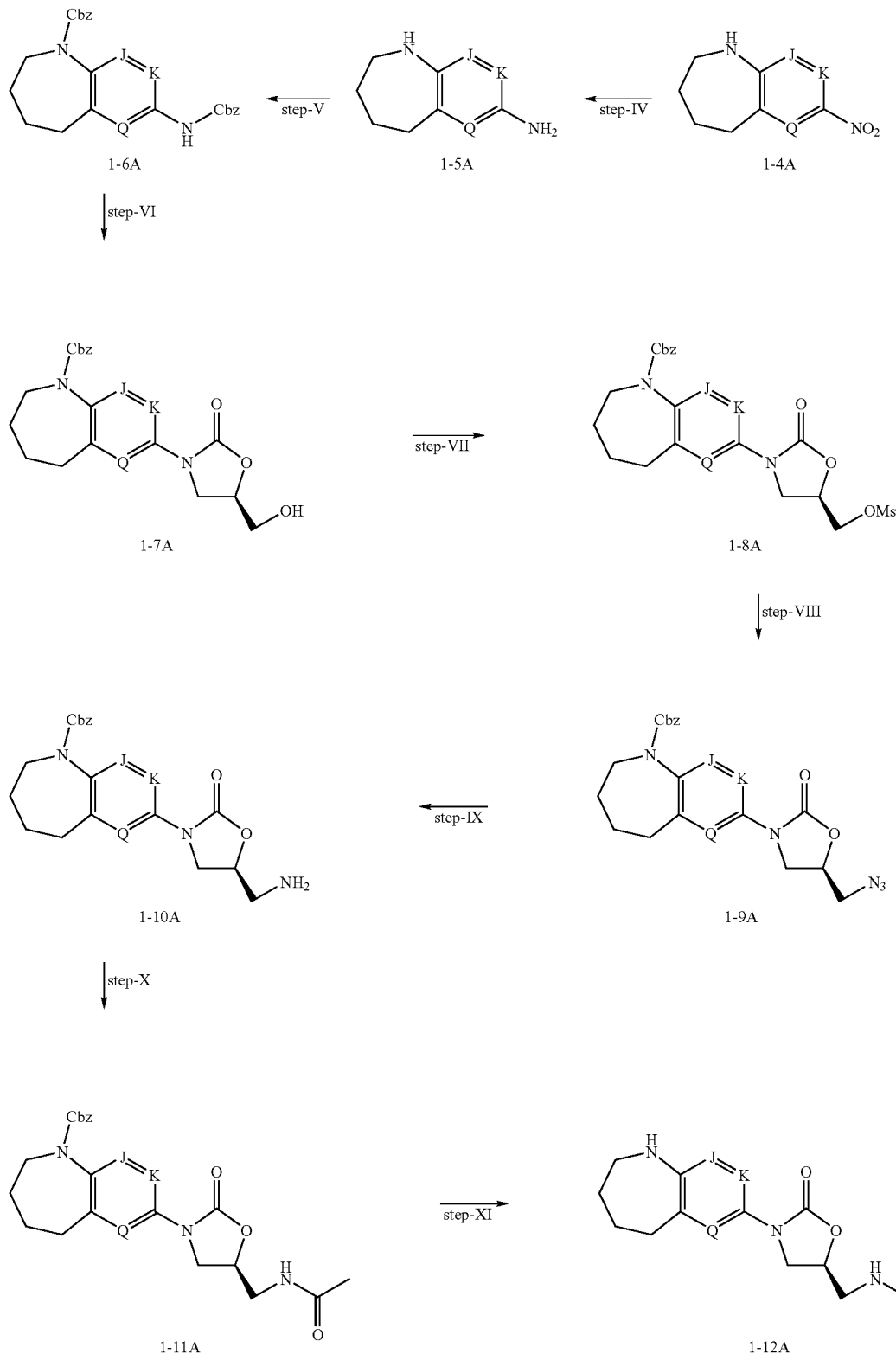

Scheme 2 provides an approach to amide 1-3A in a minimum of steps. Thus, the brominated analogue is coupled to the oxazolidinone core (step I) as outlined in Scheme 1. Deprotection (step II) provides the target compound 9B-3.

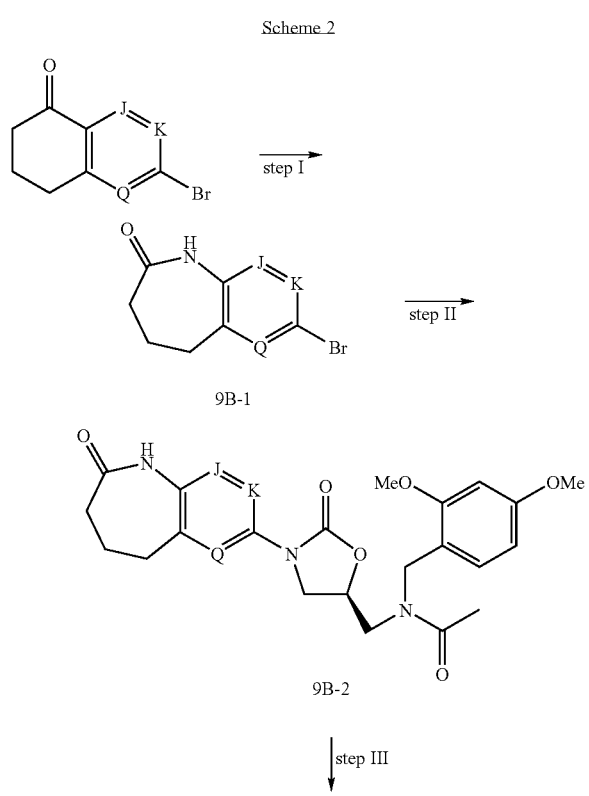

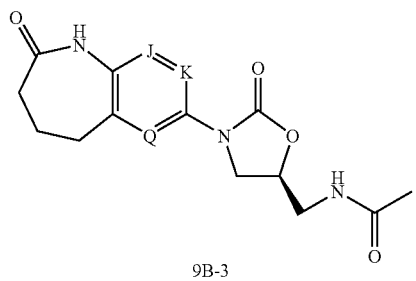

Scheme 3 provides approaches to bicyclo subunits containing N-linkages, wherein the N is "walked" around the ring to the 2- and 3-positions. Hofmann-type ring enlargement of chromanone analogue 3-1(step I) provides a mixture of amide products 3-2A and 3-2B. Upon separation, 3-2A and 3-2B are converted to target compounds 3-10A and 3-10B via a multistep sequence commencing with reduction of the amide moiety (step II); protection (step III); and attachment of the oxazolidinone subunit (step IV) to provide compounds 3-5A and 3-5B. The acetamide side chain of the oxazolidinone subunit is then elaborated (steps V/V'-VIII/VIII'), using the chemistry described for Scheme 1 to provide the target compounds 3-9A and 3-9B, which are deprotected (step IX) to provide the target compound 3-10A and 3-10B.

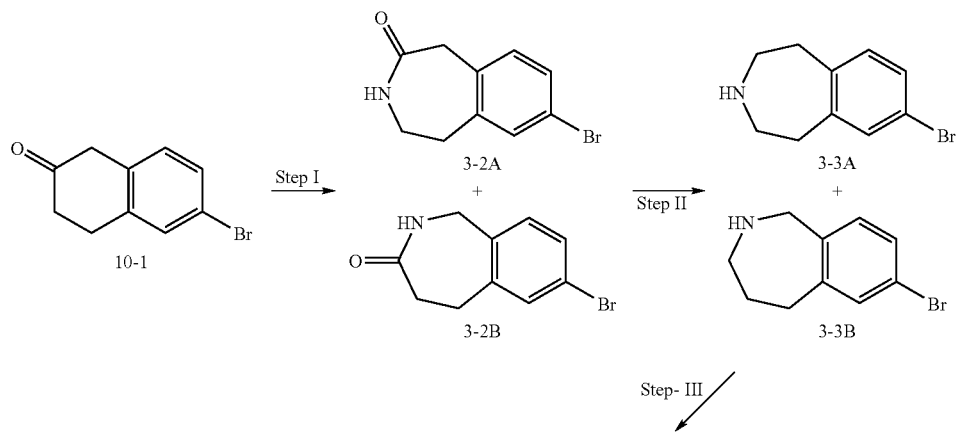

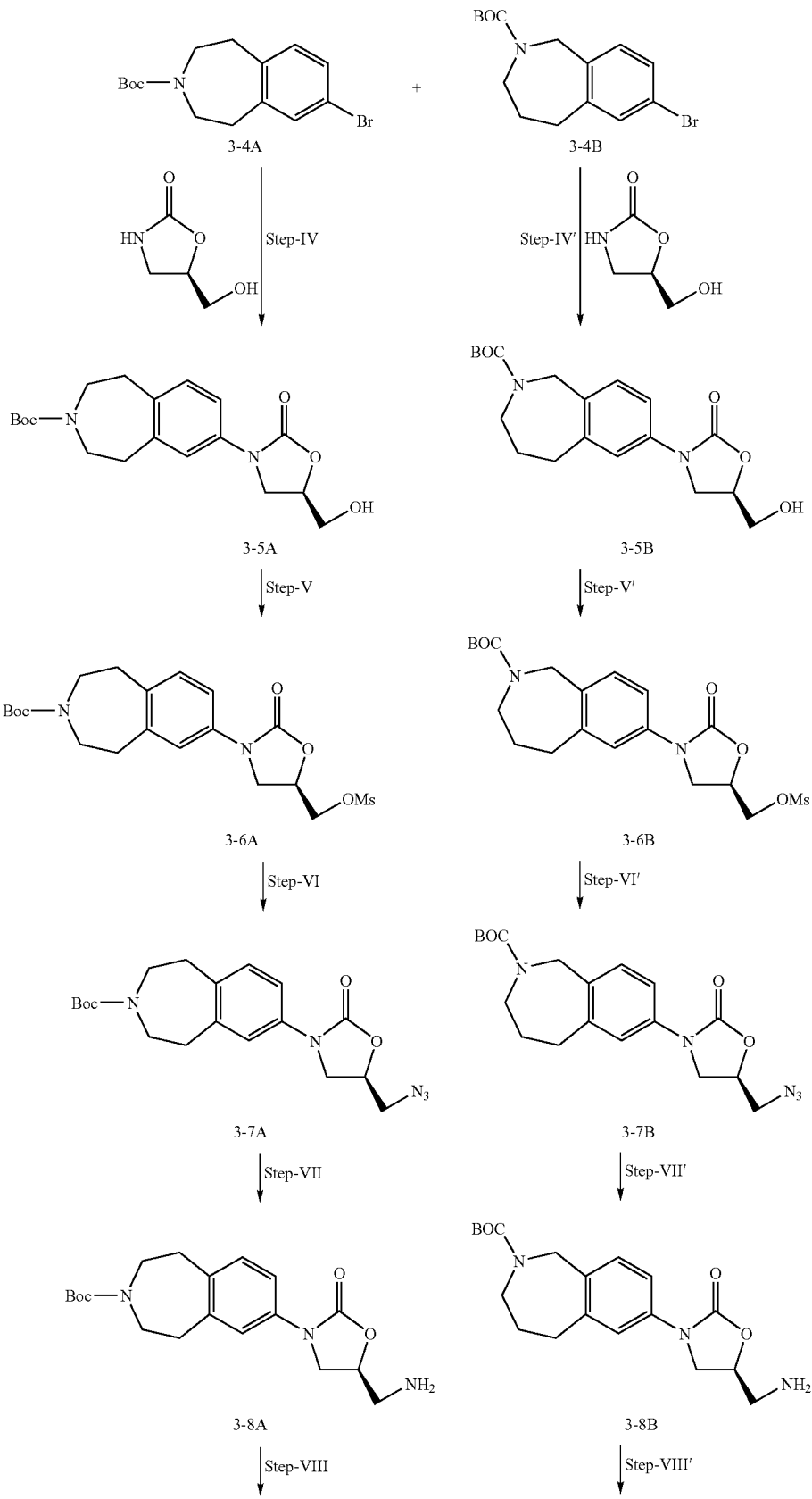

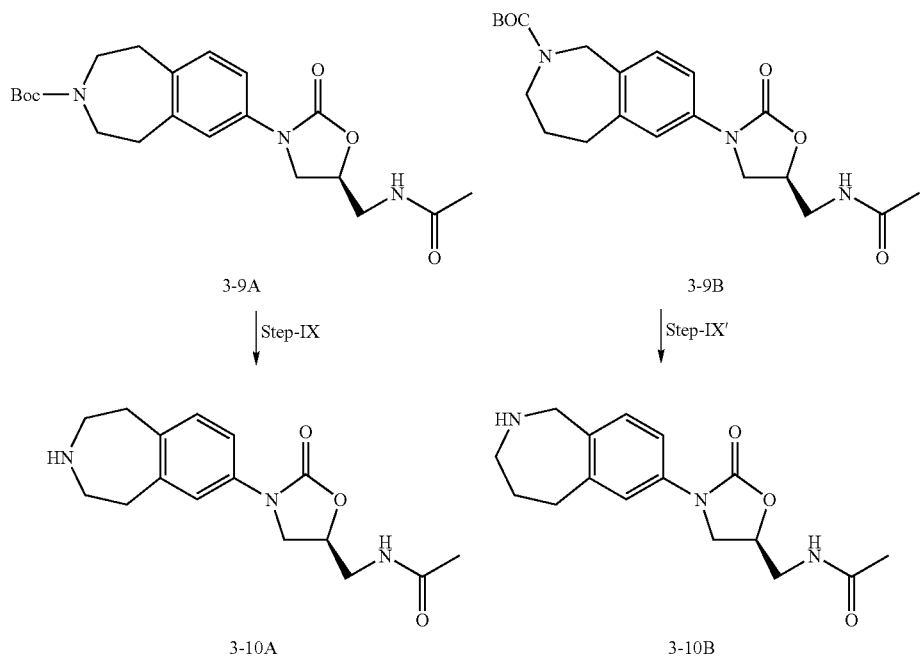

2. Subunits wherein $Z_2$ is

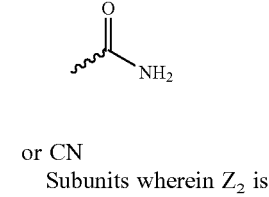

or CN

Subunits wherein $Z_2$ is

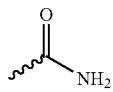

or CN can be prepared as provided in Scheme 4. Thus, azepin 1 can be protected as the amide using methods available to the skilled artisan. It is important to note that the nitrogen atom of the azepine can be occupy any position (the 1- through the 5- positons) of the azepine ring. Nitration of compound 2 provides compound 3, which is subsequently hydrogenated to afford amine 4. Construction of the oxazolidinone ring is constructed from the amine moiety in compound 4 and reagents known to the skilled artisan to provide compound 5. The ester moiety in compound 5 is then converted to an amide moiety using methanol and ammonia to give compound 6. Compound 6 can then be converted to nitrile 7 using a dehydration agent.

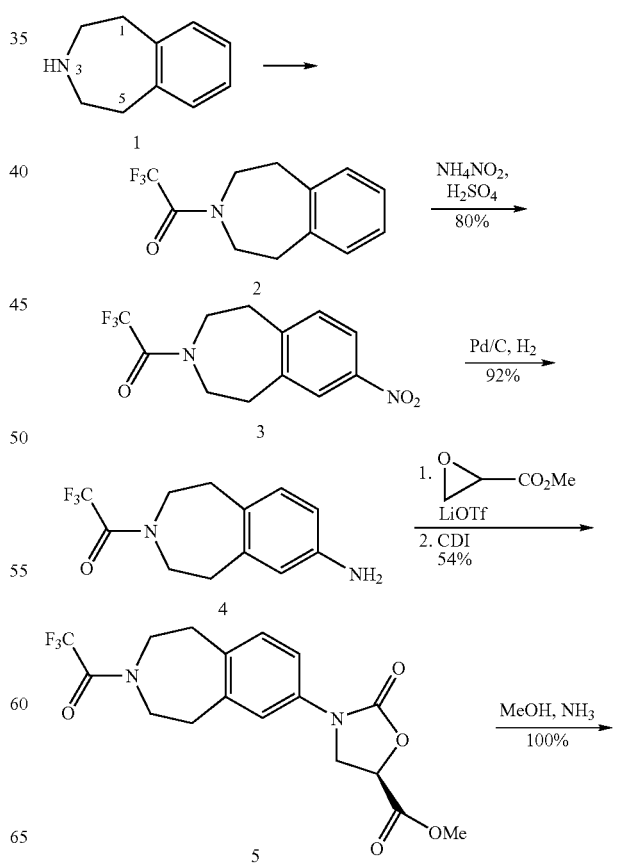

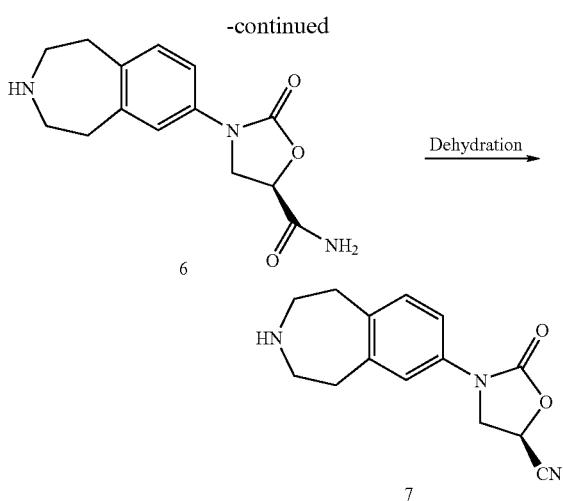

B. Preparation of Quinone-Oxazolidinone Invention Compounds

As depicted in Scheme I, invention compounds are prepared by coupling an appropriately substituted quinone

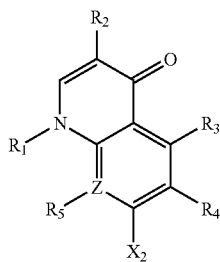

wherein X is halo, triflate or a similar leaving group known to the skilled artisan and $R_2$ is a borate ester $CO_2$-$BF_2$, is combined with an azepine-oxazolidinone subunit and triethylamine, in acetonitrile. The mixture is typically heated at 60° C. for 1 or more days. The mixture is then cooled to room temperature and concentrated. The residue is chromatographed over silica gel, typically eluting with MeOH in dichloromethane, to give the intermediate borate ester. This material is suspended in excess triethylamine, ethanol, and water. The mixture is refluxed for 1 to 2 days. The mixture is then cooled to room temperature and concentrated. The residue is partitioned between dichloromethane and water. The organic layer is washed with brine, dried ($MgSO_4$), and concentrated to give the invention compound, which can be further purified by recrystallization, typically from EtOH-ether.

Pharmaceutical Formulations

The present invention also provides pharmaceutical compositions which comprise a bioactive invention compound or a salt such as a pharmaceutically acceptable salt thereof and optionally a pharmaceutically acceptable carrier. The compositions include those in a form adapted for oral, topical or parenteral use and can be used for the treatment of bacterial infection in mammals including humans.

The compounds, such as antibiotic compounds, also referred to herein as antimicrobial compounds, according to the invention can be formulated for administration in any convenient way for use in human or veterinary medicine, by analogy with other bioactive agents such as antibiotics. Such methods are known in the art and are not described in detail herein.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present, for example, from about 1% up to about 98% of the formulation. For example, they may form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods will known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being preferred. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, e.g., from about 10-60% by weight, of the active material, depending on the method of administration. Where the compositions comprise dosage units, each unit will contain, for example, from about 50-500 mg of the active ingredient. The dosage as employed for adult human treatment will range, for example, from about 100 to 3000 mg per day, for instance 1500 mg per day depending on the route and frequency of administration. Such a dosage corresponds to about 1.5 to 50 mg/kg per day. Suitably the dosage is, for example, from about 5 to 20 mg/kg per day.

Biological Activity

The invention compounds can be screened to identify bioactive molecules with different biological activities using methods available in the art. The bioactive molecules, for example, can possess activity against a cellular target, including but not limited to enzymes and receptors, or a microorganism. A target cellular ligand or microorganism is one that is known or believed to be of importance in the etiology or progression of a disease. Examples of disease states for which compounds can be screened for biological activity include, but are not limited to, inflammation, infection, hypertension, central nervous system disorders, and cardiovascular disorders.

In one embodiment, the invention provides methods of treating or preventing an infectious disorder in a subject, such as a human or other animal subject, are provided, by administering an effective amount of an invention compound as disclosed herein to the subject. In one embodiment, the compound is administered in a pharmaceutically acceptable form optionally in a pharmaceutically acceptable carrier. As used herein, an "infectious disorder" is any disorder characterized by the presence of a microbial infection, such as bacterial infections. Such infectious disorders include, for example central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, may be adjusted as needed.

The compounds of the invention may be used for the treatment or prevention of infectious disorders caused by a variety of bacterial organisms. Examples include Gram positive and Gram negative aerobic and anaerobic bacteria, including *Staphylococci*, for example *S. aureus*; *Enterococci*, for example *E. faecalis*; *Streptococci*, for example *S. pneumoniae*; *Haemophilus*, for example *H. influenza*; *Moraxella*, for example *M. catarrhalis*; and *Escherichia*, for example *E. coli*. Other examples include *Mycobacteria*, for example *M. tuberculosis*; intercellular microbes, for example *Chlamydia* and *Rickettsiae*; and *Mycoplasma*, for example *M. pneumoniae*.

The ability of a compound of the invention to inhibit bacterial growth, demonstrate in vivo activity, and enhanced pharmacokinetics are demonstrated using pharmacological models that are well known to the art, for example, using models such as the tests described below.

Test A—Antibacterial Assays

The compounds of the present invention were tested against an assortment of Gram-negative and Gram-positive organisms using standard microtitration techniques (Cohen et. al., *Antimicrob.*, 1985;28:766;Heifetz, et. al., *Antimicrob.*, 1974;6: 124). The results of the evaluation are shown in Tables 1A and B.

TABLE 1A

| | Minimum Inhibitory Concentrations μg/mL Gram Negative Bacteria | | |
|---|---|---|---|
| Compound No. or Example No. | H. influenzae HI3542 | M. catarrhalis BC3534 | E. coli Tol C |
| 12 | 0.06 | 0.25 | 4 |
| 13 | 0.06 | 1 | 4 |
| 14 | 0.06 | 2 | 16 |
| 15 | 0.06 | 4 | 4 |
| 16 | 0.125 | 16 | 64 |
| 1 | 0.06 | 0.25 | 2 |
| 2 | 0.06 | 8 | 16 |
| 11 | 0.06 | 0.5 | 8 |
| 3 | 0.06 | 16 | 32 |
| 4 | 0.06 | 0.5 | 2 |
| 6 | 0.06 | 0.13 | 2 |
| 5 | 0.06 | 2 | 8 |
| 7 | 0.06 | 0.25 | 2 |
| 8 | 0.06 | 2 | 2 |
| 9 | 0.06 | 0.5 | 4 |
| 10 | 0.06 | 0.13 | 1 |
| 17 | 0.5 | 64 | 64 |
| 18 | 0.06 | 2 | 16 |

TABLE 1B

| Compound | Minimum Inhibitory Concentrations μg/mL Gram Positive Bacteria | | |
|---|---|---|---|
| Structure or Example No. | E. faecalis MGH-2 | S. aureus UC-76 | S pyogenes C203 |
| 12 | 1 | 0.25 | 1 |
| 13 | 8 | 0.5 | 2 |
| 14 | 16 | 0.5 | 8 |
| 15 | 4 | 2 | 4 |
| 16 | 32 | 8 | 4 |
| 1 | 1 | 0.06 | 2 |
| 2 | 8 | 0.06 | 8 |
| 11 | 8 | 0.06 | 16 |
| 3 | 32 | 1 | 16 |
| 4 | 1 | 0.06 | 1 |
| 6 | 0.25 | 0.06 | 0.25 |
| 5 | 32 | 1 | 8 |
| 7 | 0.5 | 0.06 | 1 |
| 8 | 16 | 0.5 | 8 |
| 9 | 8 | 0.13 | 4 |
| 10 | 0.25 | 0.06 | 0.25 |
| 17 | 64 | 64 | 64 |
| 18 | 8 | 1 | 0.06 |

The compounds of the present invention were tested against *E. coli* transcription and translation (TnT) assay. The TnT assay is a cell free system that utilizes an *E. coli* S30 fraction and a "premix" to transcribe and translate the firefly luciferase gene from an exogenously supplied plasmid DNA. The amount of luciferase produced is measured by observing the luminescence produced after addition of a luciferase assay reagent. The TnT assay reagents, including the luciferase reporter plasmid pBESTluc, were purchased from Promega Corporation. The protocol was based upon the manufacturer's instructions (Promega Technical Bulletin number 92 "*E. coli* S30 Extract System for Circular DNA"). Luciferase assay reagent (LucLite Plus) was purchased from Packard Biosciences.

The assay was conducted in white, flat-bottomed, polystyrene 96-well plates. Each well contained S30, premix, amino acids, compound and DNA in a total volume of 35 microliters. The reactions were allowed to incubate at room temperature for 20 minutes, then quenched with 35 microliters of LucLite Plus. The plate was then sealed with an aluminum foil lid and allowed to mix on a plate shaker for five minutes. The plate was then uncovered and read on the LJL Analyst using the standard luminescence protocol. The assay can also be read with a Perkin-Elmer Microbeta Trilux using a 1450-105 96 well plate cassette utilizing a protocol with a 10 second counting time, no background correction, and upper PMT usage. The results of the evaluation are shown in Table 1C.

TABLE 2C

| Compound Structure or Example No. | Minimum Inhibitory Concentrations µg/mL *E. coli* TnT Assay |
|---|---|
| 12 | 9.3 |
| 13 | 0.6 |
| 14 | 15 |
| 15 | 15 |
| 16 | 10 |
| 1 | 9.4 |
| 2 | 9.6 |
| 11 | 10 |
| 3 | — |
| 4 | 4.0 |
| 6 | 9.6 |
| 5 | 22.4 |
| 7 | 11.8 |
| 8 | 23.0 |
| 9 | 13.0 |
| 10 | 5.4 | the following example are provided to illustrate but not limit the claimed invention.

EXAMPLE 1

7-{7-[5-(Acetylamino-methyl)-2-oxo-oxazolidin-3-yl]-1,3,4,5-tetrahydro-benzo[c]azepin-2-yl}-8-chloro-1-cyclopropyl-6-fluoro-4-oxo-1,4-dihydro-quinoline-3-carboxylic Acid A mixture of 0.16 g (0.46 mmol) of 8-chloro-1-cyclopropyl-6,7-difluoro-4-oxo-1,4-dihydro-4-oxo-1,4-dihydro-quinoline-3-carboxylic acid boron difluoride chelate (prepared as in European Patent Application 0352123, 1989; Chem. Abstr. 1990, 113, 78178k), 0.14 g (0.46 mmol) of N-[2-oxo-3-(2,3,4,5-tetrahydro-1H-benzo[c]azepin-7-yl)-oxazolidin-5-ylmethyl]-acetamide, 0.14 g (1.4 mmol) of triethylamine, and acetonitrile (10 mL) was heated at 60° C. for 2 days. The mixture was cooled to room temperature and concentrated. The residue was chromatographed over silica gel, eluting with 10% MeOH in dichloromethane, to give the intermediate borate ester. This material was suspended in 10 equivalents of triethylamine, ethanol (EtOH)(10 mL) and water (0.5 mL) and was refluxed for 18 hours. The mixture was cooled to room temperature and concentrated. The residue was partitioned between dichloromethane and water. The organic layer was washed with brine, dried (MgSO$_4$), and concentrated to give the title compound, which was recrystallized from EtOH-ether. MS (APCI): AP+, 583.2. NMR (CDCl$_3$)0.94 (m, 2 H), 1.27 (m, 2 H), 1.99 (m plus s, 5 H total), 3.03 (m, 2 H), 3.57 (m, 3 H), 3.66-3.77 (m, 2 H), 4.03 (t, 1 H), 4.29 (m, 1 H), 4.40 (s, 2 H), 4.73 (m, 1 H), 5.94 (br t, 1 H), 7.02 (d, J=8Hz, 1 H), 7.20 (m, partially obscured by solvent, 1 H), 7.38(d, J=2Hz, 1 H), 8.00 (d, J=11Hz, 1 H), 8.87 (s, 1 H).

EXAMPLE 2

7-{7-[5-(Acetylamino-methyl)-2-oxo-oxazolidin-3-yl]-1,3,4,5-tetrahydro-benzo[c]azepin-2-yl}-1-cyclopropyl-6-fluoro-8-methoxy-5-methyl-4-oxo-1,4-dihydro-quinoline-3-carboxylic Acid The title compound was prepared in a procedure analogous to that used in Example 1, using 1-cyclopropyl-6,7-difluoro-8-methoxy-5-methyl-4-oxo-1,4-dihydro-quinoline-3-carboxylic acid boron difluoride chelate. MS (APCI) AP+, 593.2. NMR (CDCl$_3$)0.85 (m, 2 H), 1.14-1.19 (m, 2 H), 1.99 (s plus m, 5 H), 2.72 (d, J=3Hz, 3 H), 3.05 (m, 2 H), 3.35 (s, 3 H), 3.54-3.59 (m, 1 H), 3.67-3.77 (m, 4 H), 3.98-4.05 (m plus q, 2 H), 4.47 (s, 2 H), 4.7 (m, 1 H), 5.88 (br t, 1 H), 7.07 (d, J=8.3Hz, 1 H), 7.21 (m, partially obscured by CDCl3, 1 H), 7.37 (d, J=2.2Hz, 1 H), 8.74 (s, 1 H)

EXAMPLE 3

7-{7-[5-(Acetylamino-methyl)-2-oxo-oxazolidin-3-yl]-1,3,4,5-tetrahydro-benzo[c]azepin-2-yl}-1-cyclopropyl-6-fluoro-5-methyl-4-oxo-1,4-dihydro-quinoline-3-carboxylic Acid The title compound was prepared in a procedure analogous to that used in Example 1, using 1-cyclopropyl-6,7-difluoro -5-methyl-4-oxo-1,4-dihydro-quinoline-3-carboxylic acid boron difluoride chelate. MS (APCI) AP+, 563.2 NMR (DMSO)1.01 (m, 2 H), 1.20 (m, 2 H), 1.75 (s, 3 H), 1.93 (m, 2 H), 2.69 (d, J=3Hz, 3 H), 3.01 (m, 2 H), 3.33 (m, partially obscured by water), 3.60-3.64 (m, 2 H), 3.90 (m, 2 H), 4.00 (t, 1 H), 4.59-4.64 (m, 1 H), 4.75 (s, 2 H), 7.20-7.27 (m, 2 H), 7.34 (m, 1 H), 8.14 (t, 1 H), 8.80 (s, 1 H).

EXAMPLE 4

7-{7-[5-(Acetylamino-methyl)-2-oxo-oxazolidin-3-yl]-1,3,4,5-tetrahydro-benzo[c]azepin-2-yl}-1-cyclopropyl-6-fluoro-8-methoxy-4-oxo-1,4-dihydro-quinoline-3-carboxylic Acid The title compound was prepared in a procedure analogous to that used in Example 1, using 1-cyclopropyl-6,7-difluoro-8-methoxy-4-oxo-1,4-dihydro-quinoline-3-carboxylic acid boron difluoride chelate. The product was purified via trituration with ether. MS (APCI) AP+, 579.2. NMR (CDCl$_3$) 1.00(m, 2 H), 1.15-1.24 (m, 2 H), 1.99 (m plus s, 5 H), 3.03 (m, 2 H), 3.43 (s, 3 H), 3.53-3.59 (m, 1 H), 3.66-3.77 (m, 4 H), 3.97-4.05 (m, 2 H), 4.46 (s, 2 H), 4.70-4.75 (m, 1 H), 5.90 (br t, 1 H), 7.07 (d, J=8.3 Hz, 1 H), 7.19 (m, partially obscured by solvent, 1 H), 7.37 (d, 1 H), 7.82 (d, J=12 Hz, 1 H), 8.78 (s, 1 H).

EXAMPLE 5

9-{7-[5-(Acetylamino-methyl)-2-oxo-oxazolidin-3-yl]-1,3,4,5-tetrahydro-benzo[c]azepin-2-yl}-8-fluoro-3-methyl-6-oxo-2,3-dihydro-6 H-1-oxa-3a-aza-phenalene-5-carboxylic Acid The title compound was prepared in a procedure analogous to that used in Example 1, using 8,9-difluoro-3-methyl-6-oxo-2,3-dihydro-6 H-1-oxa-3a-aza-phenalene-5-carboxylic acid boron difluoride chelate. The product was purified via trituration with EtOH. MS (APCI) AP+, 565.2. NMR (CDCl$_3$)1.58 (d, J=6.8 Hz, 3 H), 1.98 (m plus s, 5 H), 3.01 (br t, 2 H), 3.54-3.57 (m, 1 H), 3.60-3.77 (m, 4 H), 4.02 (t, 1 H), 4.27 (m, 1 H), 4.34-4.46 (m, 4 H), 4.73 (m, 1 H), 5.93 (br t, 1 H), 7.00 (d, J=8.3 Hz, 1 H), 7.20 (m, 1 H), 7.35 (m, 1 H), 7.69 (d, J=12.2 Hz, 1 H), 8.55 (s, 1 H).

EXAMPLE 6

7-{7-[5-(Acetylamino-methyl)-2-oxo-oxazolidin-3-yl]-1,2,4,5-tetrahydro-benzo[d]azepin-3-yl}-1-cyclopropyl-6-fluoro-8-methoxy-5-methyl-4-oxo-1,4-dihydro-quinoline-3-carboxylic Acid A mixture of 0.12 g (0.34 mmol) of 1-cyclopropyl-6,7-difluoro-8-methoxy-5-methyl-4-oxo-1,4-dihydro-quinoline-3-carboxylic acid boron difluoride chelate, 0.10 g (0.34 mmol) of N-[2-oxo-3-(2,3,4,5-tetrahydro-1 H-benzo[d]azepin 7-yl)-oxazolidin-5-ylmethyl]-acetamide, 0.10 g (1.0 mmol) of triethylamine, and acetonitrile (10 mL) was heated at 60° C. for 2 days. The mixture was cooled to room temperature and concentrated. The residue was chromatographed over silica gel, eluting with 10% MeOH in dichloromethane, to give the intermediate borate ester. This material was suspended in 10 equivalents of triethylamine, EtOH (10 mL) and water (0.5 mL) and was refluxed for 18 hours. The mixture was cooled to room temperature and concentrated. The residue was partitioned between dichloromethane and water. The organic layer was washed with brine, dried (MgSO$_4$), and concentrated. The title compound was isolated via silica gel chromatography, eluting with 10% MeOH in CH$_2$Cl$_2$. MS (APCI): AP+, 593.2. NMR (CDCl$_3$) 0.83 (m, 2 H), 1.13 (m, 2 H), 2.00 (s, 3 H), 2.74 (d, J=3 Hz, 3 H), 3.08 (m, 4 H), 3.44 (m, 5 H), 3.58 (s plus m, 4 H), 3.67-3.71 (m, 1 H), 3.75-3.79 (m, 1 H), 3.98-4.06 (m plus t, 2 H), 4.75 (m, 1 H), 5.97 (br t, 1 H), 7.13 (d, J=8.3 Hz, 1 H), 7.20 (m, partially obscured by CDCl3, 1 H), 7.38 (m, 1 H), 8.75 (s, 1 H).

EXAMPLE 7

7-{7-[5-(Acetylamino-methyl)-2-oxo-oxazolidin-3-yl]-1,2,4,5-tetrahydro-benzo[d]azepin-3-yl}-1-cyclopropyl-6-fluoro-8-methoxy-4-oxo-1,4-dihydro-quinoline-3-carboxylic Acid The title compound was prepared in a procedure analogous to that used in Example 6, using 1-cyclopropyl-6,7-difluoro-8-methoxy-4-oxo-1,4-dihydro-quinoline-3-carboxylic acid boron difluoride chelate. MS (APCI) AP+, 579.2 NMR (CDCl$_3$)0.98 (m, 2 H), 1.15-1.22 (m, 2 H), 2.00 (s, 3 H, acetyl), 3.08 (br t, 4 H), 3.45 (m, 4 H), 3.54-3.60 (m, 1 H), 3.69 (m plus s, 4 H total), 3.72-3.78 (m, 1 H), 3.97-4.06 (m plus t, 2 H), 4.71-4.76 (m, 1 H), 5.91 (br t, 1 H), 7.13 (d, J=8.3 Hz, 1 H), 7.20 (m, partially obscured by solvent, 1 H), 7.38 (m, 1 H), 7.87 (d, J=11.7 Hz, 1 H), 8.78 (s, 1 H).

EXAMPLE 8

7-{7-[5-(Acetylamino-methyl)-2-oxo-oxazolidin-3-yl]-1,2,4,5-tetrahydro-benzo[d]azepin-3-yl}-1-(2,4-difluoro-phenyl)-6-fluoro-4-oxo-1,4-dihydro-[1,8]naphthyridine-3-carboxylic Acid The title compound was prepared in a procedure analogous to that used in Example 6, using 7-chloro-1-(2,4-difluoro-phenyl)-6-fluoro-4-oxo-1,4-dihydro-[1,8]naphthyridine-3-carboxylic acid boron difluoride chelate. The product was purified via silica gel chromatography, eluting with 10% MeOH in CH$_2$Cl$_2$. MS (APCI) AP+, 622.2. NMR (CDCl$_3$)1.98 (s, 3 H), 2.80 (m, 4 H), 3.53-3.60 (m, 1 H), 3.65-3.74 (m, 6 H), 3.96-4.01 (m, 1 H), 4.69-4.75 (m, 1 H), 5.91 (br t, 1 H), 7.09 (m, 1 H), 7.13 (m, 3 H), 7.32 (m, 1 H), 7.36-7.42 (m, 1 H), 8.08 (d, J=14.4 Hz, 1 H), 8.63 (s, 1 H).

EXAMPLE 9

7-{7-[5-(Acetylamino-methyl)-2-oxo-oxazolidin-3-yl]-1,2,4,5-tetrahydro-benzo[d]azepin-3-yl}-1-cyclopropyl-6-fluoro-4-oxo-1,4-dihydro-quinoline-3-carboxylic Acid The title compound was prepared in a procedure analogous to that used in Example 6, using 1-cyclopropyl-6,7-difluoro-4-oxo-1,4-dihydro-quinoline-3-carboxylic acid boron difluoride chelate. MS (APCI) AP+, 549.2 NMR (CDCl$_3$)1.10-1.17 (m, 2 H), 1.29-1.34 (m, 2 H), 1.93 (s, 3 H), 3.05-3.10 (m, 4 H), 3.44-3.51 (m, 1 H), 3.54-3.60 (m, 6 H), 3.71-3.75 (m, 1H), 3.96(t, 1 H), 4.69 (m, 1 H), 6.78 (br t, 1 H), 7.08 (d, 1 H), 7.17 (m, 1 H), 7.26 (m, partially obscured by solvent, 1 H), 7.36 (s, 1 H), 7.93 (d, J=13.7 Hz, 1 H), 8.67 (s, 1 H).

EXAMPLE 10

7-{7-[5-(Acetylamino-methyl)-2-oxo-oxazolidin-3-yl]-1,2,4,5-tetrahydro-benzo[d]azepin-3-yl}-8-chloro-1-cyclopropyl-6-fluoro-4-oxo-1,4-dihydro-quinoline-3-carboxylic Acid The title compound was prepared in a procedure analogous to that used in Example 6, using 8-chloro-1-cyclopropyl-6,7-difluoro-4-oxo-1,4-dihydro-quinoline-3-carboxylic acid boron difluoride chelate. MS (APCI) AP+, 583.2 NMR (CDCl$_3$)0.95 (m, 2 H), 1.30 (m, 2 H), 2.00 (s, 3 H), 3.10-3.14 (m, 4 H), 3.40-3.45 (m, 4 H), 3.55-3.61 (m, 1 H), 3.67-3.78 (m, 2 H), 4.04 (t, 1 H), 4.33 (m, 1 H), 4.74 (m, 1 H), 5.90 (br t, 1 H), 7.13 (m, 1 H), 7.20 (m, partially obscured by solvent, 1 H), 7.38 (d, 2.2 Hz, 1 H), 8.01 (d, J=11 Hz, 1 H), 8.89 (s, 1 H).

EXAMPLE 11

7-{7-[5-(Acetylamino-methyl)-2-oxo-oxazolidin-3-yl]-1,2,4,5-tetrahydro-benzo[d]azepin-3-yl}-1-cyclopropyl-6-fluoro-5-methyl-4-oxo-1,4-dihydro-quinoline-3-carboxylic Acid The title compound was prepared in a procedure analogous to that used in Example 6, using 1-cyclopropyl-6,7- difluoro-5-methyl-4-oxo-1,4-dihydro-quinoline-3-carboxylic acid boron difluoride chelate. The product was triturated with EtOH to purify. MS (APCI) AP+, 563.2. NMR (CDCl$_3$) 1.10-1.15 (m, 2 H), 1.30-1.34 (m, 2 H), 1.99 (s, 3 H), 2.81 (d, J=3.4 Hz, 3 H), 3.07-3.13 (m, 4 H), 3.40-3.43 (m, 1 H), 3.54-3.61 (m, 5 H), 3.66-3.77 (m, 2 H), 4.02 (t, 1 H), 4.70-4.76 (m, 1 H), 5.94 (br t, 1 H), 7.11-7.22 (m, 2 H—maybe 3 H—partially obscured by CDCl 3), 7.42 (d, J=2 Hz, 1 H), 8.69 (s, 1 H).

EXAMPLE 12

7-{7-[5-(Acetylamino-methyl)-2-oxo-oxazolidin-3-yl]-1,2,4,5-tetrahydro-benzo[d]azepin-3-yl}-1-cyclopropyl-6,8-difluoro-4-oxo-1,4-dihydro-quinoline-3-carboxylic Acid The title compound was prepared in a procedure analogous to that used in Example 6, using N-[2-Oxo-3-(2,3,4,5-tetrahydro-1 H-benzo[d]azepin-7-yl)-oxazolidin-5-ylmethyl]-acetamide (0.25 g) and 1-Cyclopropyl-6,7,8-trifluoro-4-oxo-1,4-dihydro-quinoline-3-carboxylic acid (0.23 g). The product was triturated with EtOH to purify. MS (APCI) AP+, 567. NMR (DMSO$_6$)1. 1-1.22 (m, 4H), 1.78 (s, 3H), 3.0 (m, 4H), 3.35 (m, 6H), 3.65 (m, 1H), 4.05 (m, 2H), 4.65 (m, 1H), 7.13 (d, 1H), 7.26 (dd, 1H), 7.35 (d, 1H), 7.78 (d, 1H), 8.17 (t, 1H), 8.62 (s, 1H).

EXAMPLE 13

7-{7-[5-(Acetylamino-methyl)-2-oxo-oxazolidin-3-yl]-1,3,4,5-tetrahydro-benzo[c]azepin-2-yl}-1-cyclopropyl-6,8-difluoro-4-oxo-1,4-dihydro-quinoline-3-carboxylic Acid The title compound was prepared in a procedure analogous to that used in Example 6, using N-[2-Oxo-3-(2,3,4,5-tetrahydro-1H-benzo[c]azepin-7-yl)-oxazolidin-5-ylmethyl]-acetamide (0.25 g) and 1-Cyclopropyl-6,7,8-trifluoro-4-oxo-1,4-dihydro-quinoline-3-carboxylic acid (0.23 g). The product was triturated with EtOH to purify. MS (APCI)AP+, 567. NMR (DMSO$_6$)1.1-1.22 (m, 4H), 1.78 (s, 3H), 1.87 (brm, 2H), 3.0 (brs, 2H), 3.38 (t, 2H), 3.7 (m, 3H), 4.04 (t, 2H), 4.43 (s, 2H), 4.61 (m, 1H), 7.13 (d, 1H), 7.26 (d, 1H), 7.35 (s, 1H), 7.78 (d, 1H), 8.2 (t, 1H), 8.61 (s, 1H).

EXAMPLE 14

7-{7-[5-(Acetylamino-methyl)-2-oxo-oxazolidin-3-yl]-1,2,4,5-tetrahydro-benzo[d]azepin-3-yl}-1-cyclopropyl-6-fluoro-4-oxo-1,4-dihydro-[1,8]naphthyridine-3-carboxylic Acid The title compound was prepared in a procedure analogous to that used in Example 6, using N-[2-Oxo-3-(2,3,4,5-tetrahydro-1H-benzo[d]azepin-7-yl)-oxazolidin-5-ylmethyl]-acetamide (0.25 g) and 1-Cyclopropyl-6,7-difluoro-4-oxo-1,4-dihydro-[1,8]naphthyridine-3-carboxylic acid (0.23 g). The product was triturated with EtOH to purify. MS (APCI) AP+, 550. NMR (DMSO$_6$)1.1 (m, 2H), 1.22 (m, 2H), 1.74 (s, 3H), 3.04 (m, 4H), 3.3 (m, 6H), 3.70 (m, 2H), 4.0 (m, 2H), 4.65 (m, 1H), 7.13 (d, 1H), 7.26 (dd, 1H), 7.35 (d, 1H), 8.0 (d, 1H), 8.14 (t, 1H), 8.52 (s, 1H).

EXAMPLE 15

7-{7-[5-(Acetylamino-methyl)-2-oxo-oxazolidin-3-yl]-1,3,4,5-tetrahydro-benzo[c]azepin-2-yl}-1-cyclopropyl-6-fluoro-4-oxo-1,4-dihydro-[1,8]naphthyridine-3-carboxylic Acid The title compound was prepared in a procedure analogous to that used in Example 6, using N-[2-Oxo-3-(2,3,4,5-tetrahydro 1H-benzo[c]azepin-7-yl)-oxazolidin-5-ylmethyl]-acetamide (0.25 g) and 1-Cyclopropyl-6,7,8-trifluoro-4-oxo-1,4-dihydro-quinoline-3-carboxylic acid (0.23 g). The product was triturated with EtOH to purify. MS (APCI) AP+, 567. NMR (DMSO$_6$)1.04 (m, 2H), 1.17 (m, 2H), 1.74 (s, 3H), 1.91 (brs, 2H), 3.0 (d, 2H), 3.26 (t, 2H), 3.61 (m, 2H), 3.96 (t, 1H), 4.17 (brs, 1H), 4.61 (m, 2H), 4.96 (s, 1H), 7.20 (d, 1H), 7.3 (d, 1H), 7.35 (d, 1H), 7.91 (d, 1H), 8.13 (t, 1H), 8.52 (s, 1H).

EXAMPLE 16

7-{7-[5-(Acetylamino-methyl)-2-oxo-oxazolidin-3-yl]-1,3,4,5-tetrahydro-benzo[c]azepin-2-yl}-1-cyclopropyl-6-fluoro-4-oxo-1,4-dihydro-quinolne-3-carboxylic Acid The title compound was prepared in a procedure analogous to that used in Example 6, using N-[2-Oxo-3-(2,3,4,5-tetrahydro-1H-benzo[c]azepin-7-yl)-oxazolidin-5-ylmethyl]-acetamide (0.3 g) and 1-Cyclopropyl-6,7-difluoro-4-oxo-1,4-dihydro-[1,8]naphthyridine-3-carboxylic acid (0.28 g). The product was triturated with EtOH to purify. MS (APCI) AP+, 549. NMR (DMSO$_6$)1.09 (m, 2H), 1.22 (m, 2H), 1.61 (s, 3H), 1.96 (brs, 2H), 3.04 (brd, 2H), 3.35 (t, 2H), 3.65 (m, 2H), 3.96 (brm, 2H), 4.0 (t, 1H), 4.61 (m, 1H), 4.78 (s, 2H), 7.22 (d, 1H), 7.26 (d, 1H), 7.35 (m, 2H), 7.74 (d, 1H), 8.13 (t, 1H), 8.52 (s, 1H).

EXAMPLE 17

7-{7-[5-(Acetylamino-methyl)-2-oxo-oxazolidin-3-yl]-1,3,4,5-tetrahydro-benzo[c]azepin-2-yl}-1-ethyl-6-fluoro-4-oxo-1,4-dihydro-[1,8]naphthyridine-3-carboxylic Acid The title compound was prepared in a procedure analogous to that used in Example 1, using 7-chloro-1-ethyl-6-fluoro-4-oxo-1,4-dihydro-[1,8]naphthyridine-3-carboxylic acid boron difluoride chelate. The product was purified via trituration with EtOH. MS (APCI) AP+, 537.2 NMR (DMSO) 1.32 (t, 3 H), 1.75 (s, 3 H), 1.90 (br m, 2 H), 3.02 (m, 2 H), 3.63 (m, 1 H), 4.00 (t, 1 H), 4.12 (m, 1 H), 4.45 (m, 2 H), 4.62 (m, 1 H), 4.93 (s, 2 H), 7.26-7.33 (m, 2 H), 7.96 (d, J=14 Hz, 1 H), 8.14 (m, 1 H), 9.32 (s, 1 H).

EXAMPLE 18

7-{7-[5-(Acetylamino-methyl)-2-oxo-oxazolidin-3-yl]-1,3,4,5-tetrahydro-benzo[c]azepin-2-yl}-1-cyclopropyl-8-difluoromethoxy-6-fluoro-4-oxo-1,4-dihydro-[1,8]naphthyridine-3-carboxylic Acid The title compound was prepared in a procedure analogous to that used in Example 1, using 1-cyclopropyl-8-difluoromethoxy-6,7-difluoro-4-oxo-1,4-dihydro-quinoline-3-carboxylic acid boron difluoride chelate. The product was purified via trituration with ether. MS (APCI) AP+, 615.2.

NMR (CDCl₃)0.97 (m, 2 H), 1.30 (m, 2 H), 1.99 (s plus m, 5 H), 3.03 (m, 2 H), 3.10 (m, 2 H), 3.54-3.70 (m, 3 H), 3.77 (m, 1 H), 4.03 (t, 1 H), 4.08 (m, 1 H), 4.44 (s, 2 H), 4.74 (m, 1 H), 5.94 (br t, 1 H), 6.18 (t, J=76 Hz, 1 H), 7.03 (d, J=8.3 Hz, 1 H), 7.42 (d, J=2 Hz, 1 H), 8.00 (d, J=11.7 Hz, 1 H), 8.81 (s, 1 H).

Formulations

The following illustrates representative pharmaceutical dosage forms, containing a compound of Formula I ("Invention Compound"), for therapeutic or prophylactic use in humans.

| (i) | Tablet | mg/tablet |
|---|---|---|
| | 'Invention Compound' | 25.0 |
| | Lactose | 50.0 |
| | Corn Starch (for mix) | 10.0 |
| | Corn Starch (paste) | 10.0 |
| | Magnesium Stearate (1%) | 3.0 |
| | | 300.0 |

The invention compound, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of pathogenic bacterial infections.

| (ii) | Tablet | mg/capsule |
|---|---|---|
| | 'Invention Compound | 10.0 |
| | Colloidal Silicon Dioxide | 1.5 |
| | Lactose | 465.5 |
| | Pregelatinized Starch | 120.0 |
| | Magnesium Stearate (1%) | 3.0 |
| | | 600.0 |

| (iii) | Preparation for Oral Solution | Amount |
|---|---|---|
| | 'Invention Compound' | 400 mg |
| | Sorbitol Solution (70% N.F.) | 40 mL |
| | Sodium Benzoate | 20 mg |
| | Saccharin | 5 mg |
| | Cherry Flavor | 20 mg |
| | Distilled Water q.s. | 100 mL |

The sorbitol solution is added to 40 mL of distilled water, and the invention compound is dissolved therein. The saccharin, sodium benzoate, flavor, and dye are added and dissolved. The volume is adjusted to 100 mL with distilled water. Each milliliter of syrup contains 4 mg of invention compound.

(iv) Parenteral Solution

In a solution of 700 mL of propylene glycol and 200 mL of water for injection is suspended 20 g of an invention compound. After suspension is complete, the pH is adjusted to 6.5 with 1 N hydrochloric acid, and the volume is made up to 1000 mL with water for injection. The Formulation is sterilized, filled into 5.0 mL ampoules each containing 2.0 mL, and sealed under nitrogen.

| | | Amount |
|---|---|---|
| (v) | Injection 1 (1 mg/mL) | |
| | 'Invention Compound' | 1.0 |
| | Dibasic Sodium Phosphate | 12.0 |
| | Monobasic Sodium Phosphate | 0.7 |
| | Sodium Chloride | 4.5 |
| | N Sodium hydroxide solution (pH adjustment to 7.0-7.5) | q.s. |
| | Water for injection | q.s. ad 1 mL |
| (vi) | Injection 2 (10 mg/mL) | |
| | 'Invention Compound' | 10.0 |
| | Dibasic Sodium Phosphate | 1.1 |
| | Monobasic Sodium Phosphate | 0.3 |
| | Polyethylene glyco 400 | 200.0 |
| | N hydrochloric acid solution (pH adjustment to 7.0-7.5) | q.s. |
| | Water for injection | q.s. ad 1 mL |
| (vii) | Injection 2 (10 mg/mL) | |
| | 'Invention Compound' | 20.0 |
| | Oleic Acid | 10.0 |
| | Trichloromonofluoromethane | 5,000.0 |
| | Dichlorodifluoromethane | 10,000.0 |
| | Dichlorotetrafluoroethane | 5,000.0. |

All patents, and patent documents are incorporated by reference herein, as though individually incorporated by reference. The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound which is:

7-{7-[5-(Acetylamino-methyl)-2-oxo-oxazolidin-3-yl]-1,3,4,5-tetrahydro-benzo[c]azepin-2-yl}-8-chloro-1-cyclopropyl-6-fluoro-4-oxo-1,4-dihydro-quinoline-3-carboxylic acid;

7-{7-[5-(Acetylamino-methyl)-2-oxo-oxazolidin-3-yl]-1,3,4,5-tetrahydro-benzo[c]azepin-2-yl}-1-cyclopropyl-6-fluoro-8-methoxy-5-methyl-4-oxo-1,4-dihydro-quinoline-3-carboxylic acid;

7-{7-[5-(Acetylamino-methyl)-2-oxo-oxazolidin-3-yl]-1,3,4,5-tetrahydro-benzo[c]azepin-2-yl}-1-cyclopropyl-6-fluoro-5-methyl-4-oxo-1,4-dihydro-quinoline-3-carboxylic acid;

7-{7-[5-(Acetylamino-methyl)-2-oxo-oxazolidin-3-yl]-1,3,4,5-tetrahydro-benzo[c]azepin-2-yl}-1-cyclopropyl-6-fluoro-8-methoxy-4-oxo-1,4-dihydro-quinoline-3-carboxylic acid;

9-{7-[5-(Acetylamino-methyl)-2-oxo-oxazolidin-3-yl]-1,3,4,5-tetrahydro-benzo[c]azepin-2-yl}-8-fluoro-3-methyl-6-oxo-2,3-dihydro-6H-1-oxa-3a-aza-phenalene-5-carboxylic acid;

7-{7-[5-(Acetylamino-methyl)-2-oxo-oxazolidin-3-yl]-1,2,4,5-tetrahydro-benzo[d]azepin-3-yl}-1-cyclopropyl-6-fluoro-8-methoxy-5-methyl-4-oxo-1,4-dihydro-quinoline-3-carboxylic acid;

7-{7-[5-(Acetylamino-methyl)-2-oxo-oxazolidin-3-yl]-1,2,4,5-tetrahydro-benzo[d]azepin-3-yl}-1-cyclopropyl-6-fluoro-8-methoxy-4-oxo-1,4-dihydro-quinoline-3-carboxylic acid;
7-{7-[5-(Acetylamino-methyl)-2-oxo-oxazolidin-3-yl]-1,2,4,5-tetrahydro-benzo[d]azepin-3-yl}-1-(2,4-difluoro-phenyl)-6-fluoro-4-oxo-1,4-dihydro-[1,8]naphthyridine-3-carboxylic acid;
7-{7-[5-(Acetylamino-methyl)-2-oxo-oxazolidin-3-yl]-1,2,4,5-tetrahydro-benzo[d]azepin-3-yl}-1-cyclopropyl-6-fluoro-4-oxo-1,4-dihydro-quinoline-3-carboxylic acid;
7-{7-[5-(Acetylamino-methyl)-2-oxo-oxazolidin-3-yl]-1,2,4,5-tetrahydro-benzo[d]azepin-3-yl}-8-chloro-1-cyclopropyl-6-fluoro-4-oxo-1,4-dihydro-quinoline-3-carboxylic acid;
7-{7-[5-(Acetylamino-methyl)-2-oxo-oxazolidin-3-yl]-1,2,4,5-tetrahydro-benzo[d]azepin-3-yl}-1-cyclopropyl-6-fluoro-5-methyl-4-oxo-1,4-dihydro-quinoline-3-carboxylic acid;
7-{7-[5-(Acetylamino-methyl)-2-oxo-oxazolidin-3-yl]-1,2,4,5-tetrahydro-benzo[d]azepin-3-yl}-1-cyclopropyl-6,8-difluoro-4-oxo-1,4-dihydro-quinoline-3-carboxylic acid;
7-{7-[5-(Acetylamino-methyl)-2-oxo-oxazolidin-3-yl]-1,3,4,5-tetrahydro-benzo[c]azepin-2-yl}-1-cyclopropyl-6,8-difluoro-4-oxo-1,4-dihydro-quinoline-3-carboxylic acid;
7-{7-[5-(Acetylamino-methyl)-2-oxo-oxazolidin-3-yl]-1,2,4,5-tetrahydro-benzo[d]azepin-3-yl}-1-cyclopropyl-6-fluoro-4-oxo-1,4-dihydro-[1,8]naphthyridine-3-carboxylic acid;
7-{7-[5-(Acetylamino-methyl)-2-oxo-oxazolidin-3-yl]-1,3,4,5-tetrahydro-benzo[c]azepin-2-yl}-1-cyclopropyl-6-fluoro-4-oxo-1,4-dihydro-[1,8]naphthyridine-3-carboxylic acid;
7-{7-[5-(Acetylamino-methyl)-2-oxo-oxazolidin-3-yl]-1,3,4,5-tetrahydro-benzo[c]azepin-2-yl}-1-cyclopropyl-6-fluoro-4-oxo-1,4-dihydro-quinoline-3-carboxylic acid;
7-{7-[5-(Acetylamino-methyl)-2-oxo-oxazolidin-3-yl]-1,3,4,5-tetrahydro-benzo[c]azepin-2-yl}-1-ethyl-6-fluoro-4-oxo-1,4-dihydro-[1,8]naphthyridine-3-carboxylic acid; or
7-{7-[5-(Acetylamino-methyl)-2-oxo-oxazolidin-3-yl]-1,3,4,5-tetrahydro-benzo[c]azepin-2-yl}-1-cyclopropyl-8-difluoromethoxy-6-fluoro-4-oxo-1,4-dihydro-[1,8]naphthyridine-3-carboxylic acid; or a pharmaceutically acceptable salt thereof.

2. A compound which is

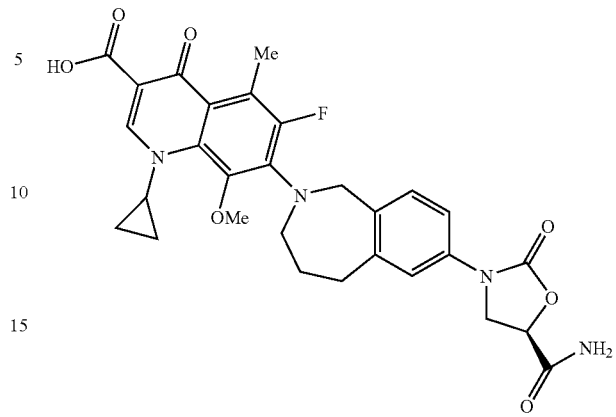

7-[7-(5-Carbamoyl-2-oxo-oxazolidin-3-yl)-1,3,4,5-tetrahydro-benzo[c]azepin-2-yl]-1-cyclopropyl-6-fluoro-8-methoxy-5-methyl-4-oxo-1,4-dihydro-quinoline-3-carboxylic acid;

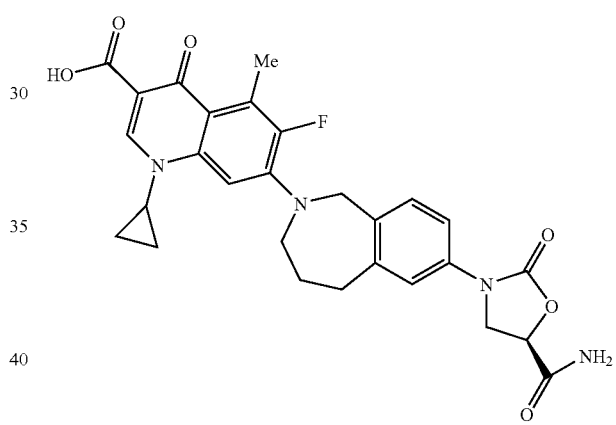

7-[7-(5-Carbamoyl-2-oxo-oxazolidin-3-yl)-1,3,4,5-tetrahydro-benzo[c]azepin-2-yl]-1-cyclopropyl-6-fluoro-5-methyl-4-oxo-1,4-dihydro-quinoline-3-carboxylic acid;

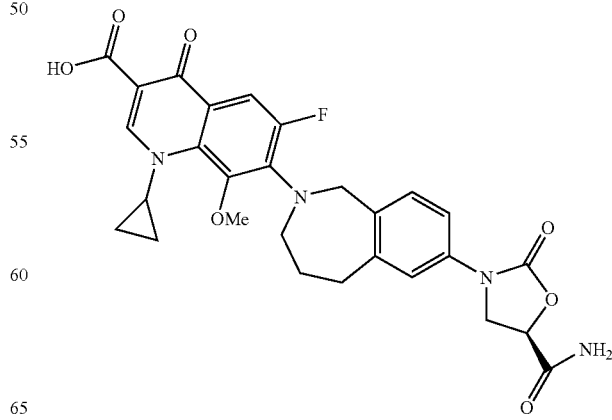

7-[7-(5-Carbamoyl-2-oxo-oxazolidin-3-yl)-1,3,4,5-tetrahydro-benzo[c]azepin-2-yl]-8-chloro-1-cyclopropyl-6-fluoro-4-oxo-1,4-dihydro-quinoline-3-carboxylic acid;

7-[7-(5-Carbamoyl-2-oxo-oxazolidin-3-yl)-1,3,4,5-tetrahydro-benzo[c]azepin-2-yl]-1-cyclopropyl-6-fluoro-8-methoxy-4-oxo-1,4-dihydro-quinoline-3-carboxylic acid;

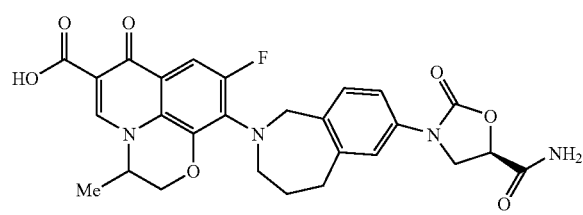

9-[7-(5-Carbamoyl-2-oxo-oxazolidin-3-yl)-1,3,4,5-tetrahydro-benzo[c]azepin-2-yl]-8-fluoro-3-methyl-6-oxo-2,3-dihydro-6H-1-oxa-3a-aza-phenalene-5-carboxylic acid;

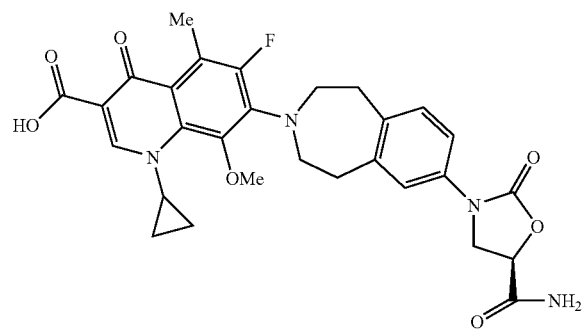

7-[7-(5-Carbamoyl-2-oxo-oxazolidin-3-yl)-1,2,4,5-tetrahydro-benzo[d]azepin-3-yl]-1-cyclopropyl-6-fluoro-8-methoxy-5-methyl-4-oxo-1,4-dihydro-quinoline-3-carboxylic acid;

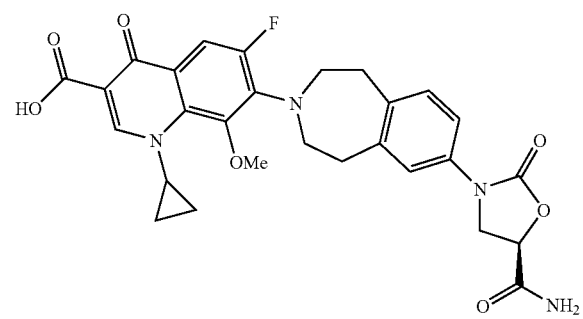

7-[7-(5-Carbamoyl-2-oxo-oxazolidin-3-yl)-1,2,4,5-tetrahydro-benzo[d]azepin-3-yl]-1-cyclopropyl-6-fluoro-8-methoxy 4-oxo-1,4-dihydro-quinoline-3-carboxylic acid;

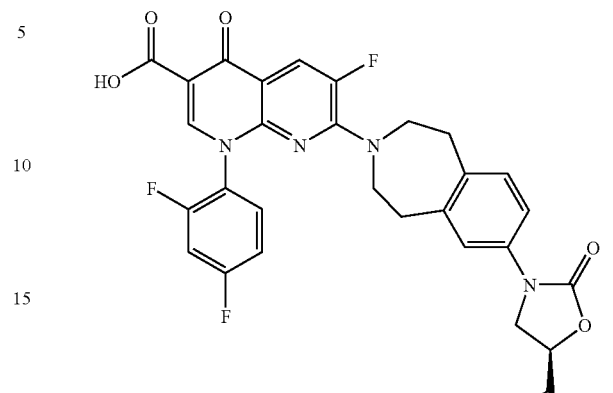

7-[7-(5-Carbamoyl-2-oxo-oxazolidin-3-yl)-1,2,4,5-tetrahydro-benzo[d]azepin-3-yl]-1-(2,4-difluoro-phenyl)-6-fluoro-4-oxo-1,4-dihydro-[1,8]naphthyridine-3-carboxylic acid;

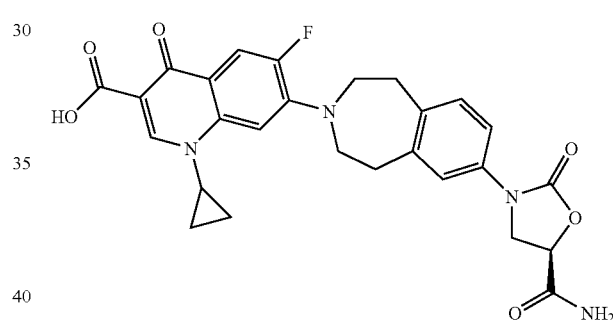

7-[7-(5-Carbamoyl-2-oxo-oxazolidin-3-yl)-1,2,4,5-tetrahydro-benzo[d]azepin-3-yl]-1-cyclopropyl-6-fluoro-4-oxo-1,4-dihydro-quinoline-3-carboxylic acid;

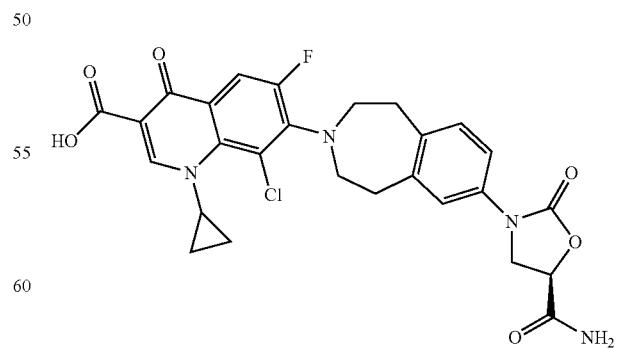

7-[7-(5-Carbamoyl-2-oxo-oxazolidin-3-yl)-1,2,4,5-tetrahydro-benzo[d]azepin-3-yl]-8-chloro-1-cyclopropyl-6-fluoro-4-oxo-1,4-dihydro-quinoline-3-carboxylic acid;

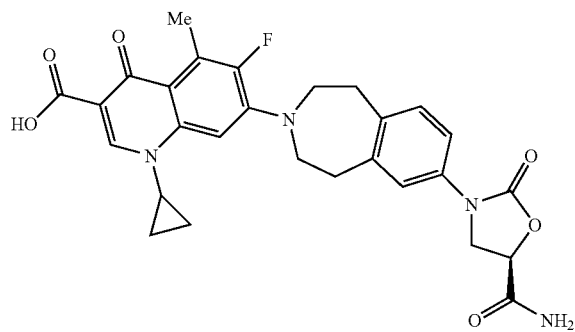

7-[7-(5-Carbamoyl-2-oxo-oxazolidin-3-yl)-1,2,4,5-tetrahydro-benzo[d]azepin-3-yl]-1-cyclopropyl-6-fluoro-5-methyl-4-oxo-1,4-dihydro-quinoline-3-carboxylic acid;

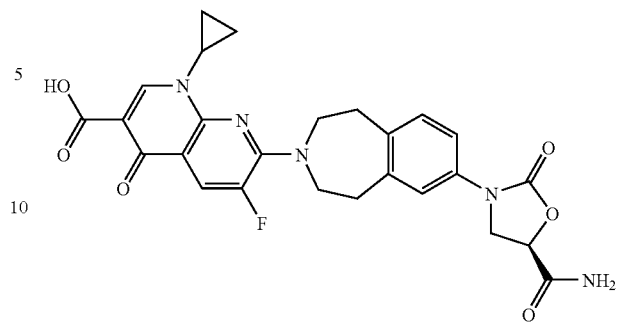

7-[7-(5-Carbamoyl-2-oxo-oxazolidin-3-yl)-1,2,4,5-tetrahydro-benzo[d]azepin-3-yl]-1-cyclopropyl-6-fluoro-4-oxo-1,4-dihydro-[1,8]naphthyridine-3-carboxylic acid;

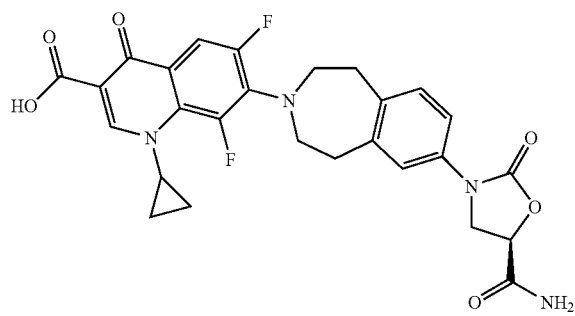

7-[7-(5-Carbamoyl-2-oxo-oxazolidin-3-yl)-1,2,4,5-tetrahydro-benzo[d]azepin-3-yl]-1-cyclopropyl-6,8-difluoro-4-oxo-1,4-dihydro-quinoline-3-carboxylic acid;

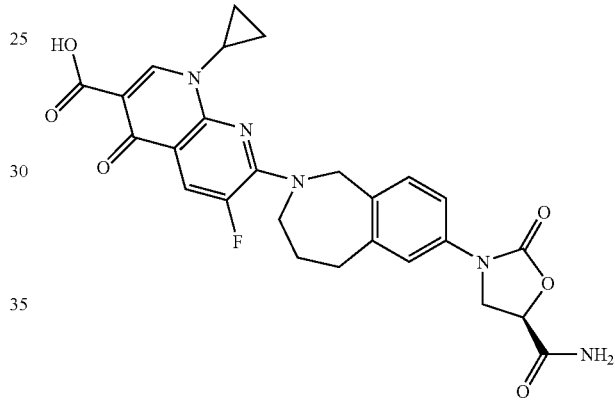

7-[7-(5-Carbamoyl-2-oxo-oxazolidin-3-yl)-1,3,4,5-tetrahydro-benzo[c]azepin-2-yl]-1-cyclopropyl-6-fluoro-4-oxo-1,4-dihydro-[1,8]naphthyridine-3-carboxylic acid;

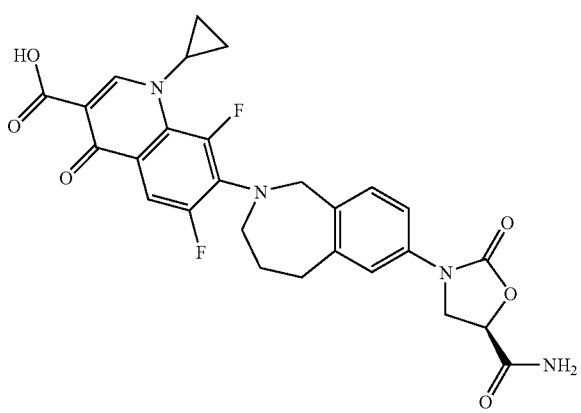

7-[7-(5-Carbamoyl-2-oxo-oxazolidin-3-yl)-1,3,4,5-tetrahydro-benzo[c]azepin-2-yl]-1-cyclopropyl-6,8-difluoro-4-oxo-1,4-dihydro-quinoline-3-carboxylic acid;

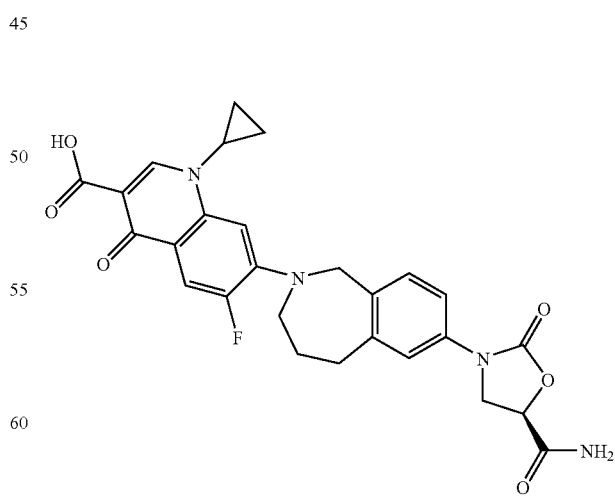

7-[7-(5-Carbamoyl-2-oxo-oxazolidin-3-yl)-1,3,4,5-tetrahydro-benzo[c]azepin-2-yl]-1-cyclopropyl-6-fluoro-4-oxo-1,4-dihydro-quinoline-3-carboxylic acid;

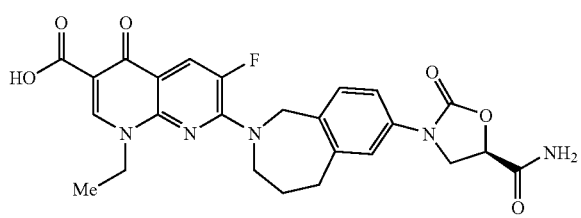

7-[7-(5-Carbamoyl-2-oxo-oxazolidin-3-yl)-1,3,4,5-tetrahydro-benzo[c]azepin-2-yl]-1-ethyl-6-fluoro-4-oxo-1,4-dihydro-[1,8]naphthyridine-3-carboxylic acid; or

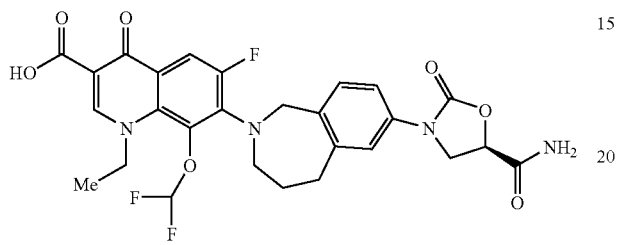

7-[7-(5-Carbamoyl-2-oxo-oxazolidin-3-yl)-1,3,4,5-tetrahydro-benzo[c]azepin-2-yl]-8-difluoromethoxy-1-ethyl-6-fluoro-4-oxo-1,4-dihydro-quinoline-3-carboxylic acid; or a pharmaceutically acceptable salt thereof.

3. A compound which is

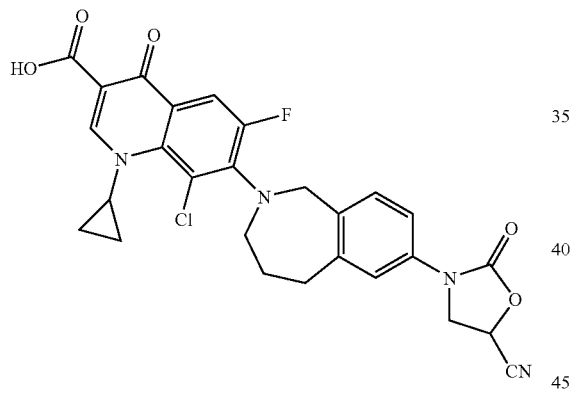

8-Chloro-7-[7-(5-cyano-2-oxo-oxazolidin-3-yl)-1,3,4,5-tetrahydro-benzo[c]azepin-2-yl]-1-cyclopropyl-6-fluoro-4-oxo-1,4-dihydro-quinoline-3-carboxylic acid;

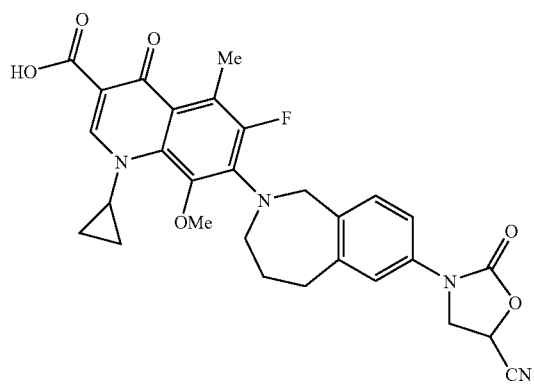

7-[7-(5-Cyano-2-oxo-oxazolidin-3-yl)-1,3,4,5-tetrahydro-benzo[c]azepin-2-yl]-1-cyclopropyl-6-fluoro-8-methoxy-5-methyl-4-oxo-1,4-dihydro-quinoline-3-carboxylic acid;

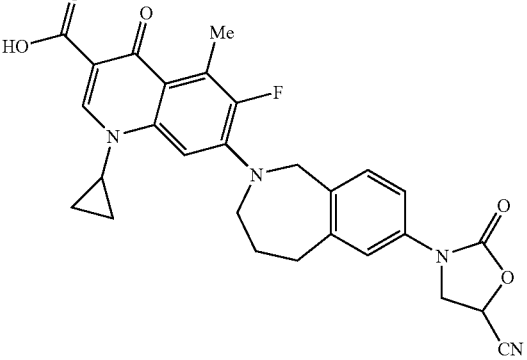

7-[7-(5-Cyano-2-oxo-oxazolidin-3-yl)-1,3,4,5-tetrahydro-benzo[c]azepin-2-yl]-1-cyclopropyl-6-fluoro-5-methyl-4-oxo-1,4-dihydro-quinoline-3-carboxylic acid;

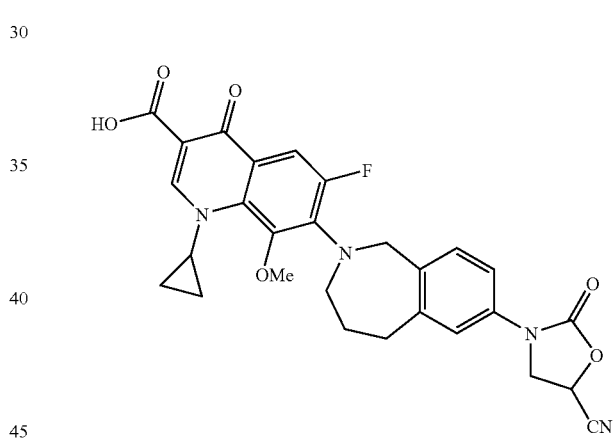

7-[7-(5-Cyano-2-oxo-oxazolidin-3-yl)-1,3,4,5-tetrahydro-benzo[c]azepin-2-yl]-1-cyclopropyl-6-fluoro-8-methoxy-4-oxo-1,4-dihydro-quinoline-3-carboxylic acid;

9-[7-(5-Cyano-2-oxo-oxazolidin-3-yl)-1,3,4,5-tetrahydro-benzo[c]azepin-2-yl]-8-fluoro-3-methyl-6-oxo-2,3-dihydro-6H-1-oxa-3a-aza-phenalene-5-carboxylic acid;

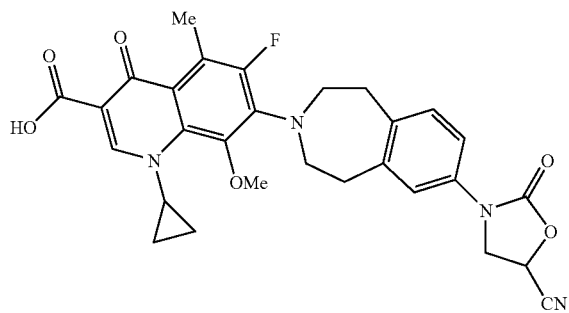

7-[7-(5-Cyano-2-oxo-oxazolidin-3-yl)-1,2,4,5-tetrahydro-benzo[d]azepin-3-yl]-1-cyclopropyl-6-fluoro-8-methoxy-5-methyl-4-oxo-1,4-dihydro-quinoline-3-carboxylic acid;

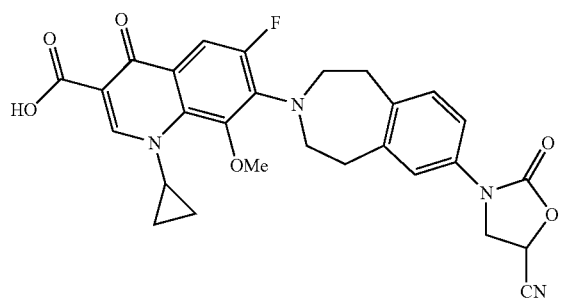

7-[7-(5-Cyano-2-oxo-oxazolidin-3-yl)-1,2,4,5-tetrahydro-benzo[d]azepin-3-yl]-1-cyclopropyl-6-fluoro-8-methoxy-4-oxo-1,4-dihydro-quinoline-3-carboxylic acid;

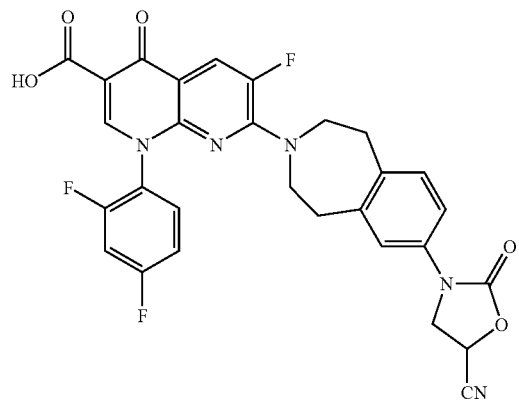

7-[7-(5-Cyano-2-oxo-oxazolidin-3-yl)-1,2,4,5-tetrahydro-benzo[d]azepin-3-yl]-1-(2,4-difluoro-phenyl)-6-fluoro-4-oxo-1,4-dihydro-[1,8]naphthyridine-3-carboxylic acid;

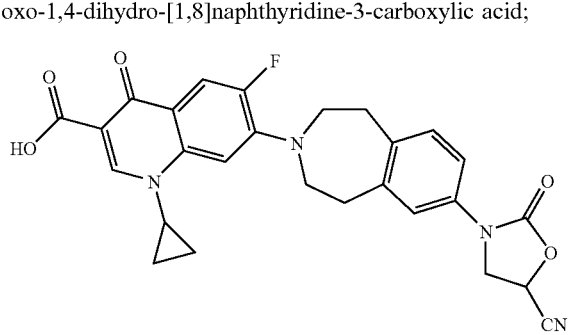

7-[7-(5-Cyano-2-oxo-oxazolidin-3-yl)-1,2,4,5-tetrahydro-benzo[d]azepin-3-yl]-1-cyclopropyl-6-fluoro-4-oxo-1,4-dihydro-quinoline-3-carboxylic acid;

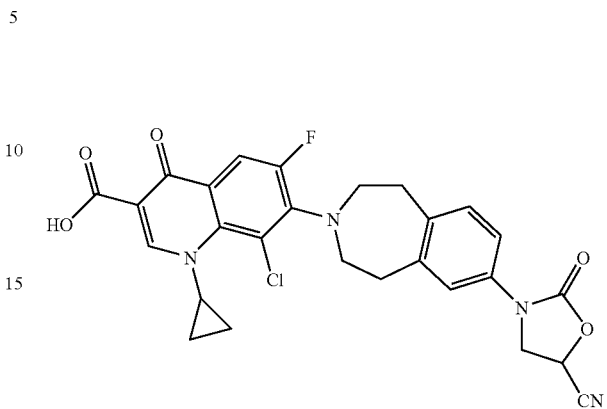

8-Chloro-7-[7-(5-cyano-2-oxo-oxazolidin-3-yl)-1,2,4,5-tetrahydro-benzo[d]azepin -3-yl]-1-cyclopropyl-6-fluoro-4-oxo-1,4-dihydro-quinoline-3-carboxylic acid;

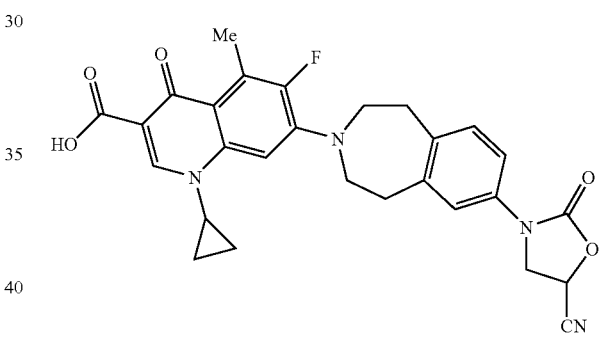

7-[7-(5-Cyano-2-oxo-oxazolidin-3-yl)-1,2,4,5-tetrahydro-benzo[d]azepin-3-yl]-1-cyclopropyl-6-fluoro-5-methyl-4-oxo-1,4-dihydro-quinoline-3-carboxylic acid;

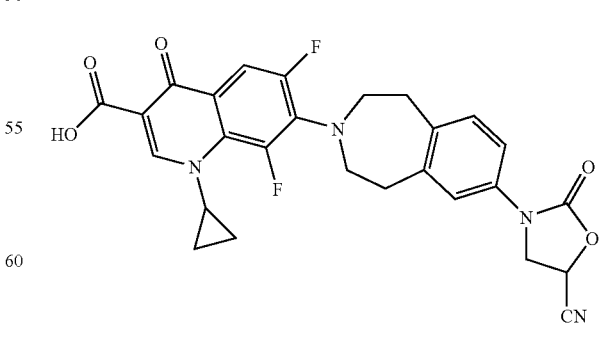

7-[7-(5-Cyano-2-oxo-oxazolidin-3-yl)-1,2,4,5-tetrahydro-benzo[d]azepin-3-yl]-1-cyclopropyl-6,8-difluoro-4-oxo-1,4-dihydro-quinoline-3-carboxylic acid;

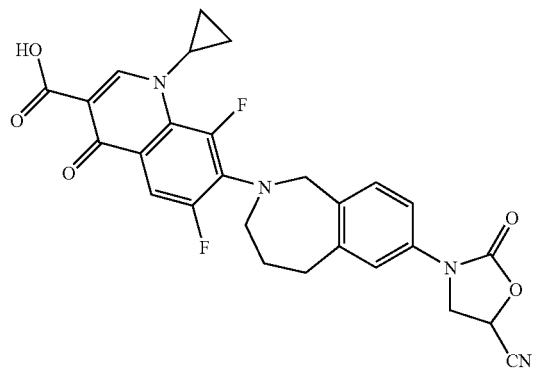

7-[7-(5-Cyano-2-oxo-oxazolidin-3-yl)-1,3,4,5-tetrahydro-benzo[c]azepin-2-yl]-1-cyclopropyl-6,8-difluoro-4-oxo-1,4-dihydro-quinoline-3-carboxylic acid;

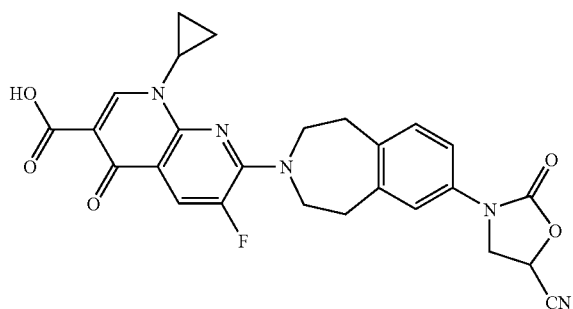

7-[7-(5-Cyano-2-oxo-oxazolidin-3-yl)-1,2,4,5-tetrahydro-benzo[d]azepin-3-yl]-1-cyclopropyl-6-fluoro-4-oxo-1,4-dihydro-[1,8]naphthyridine-3-carboxylic acid;

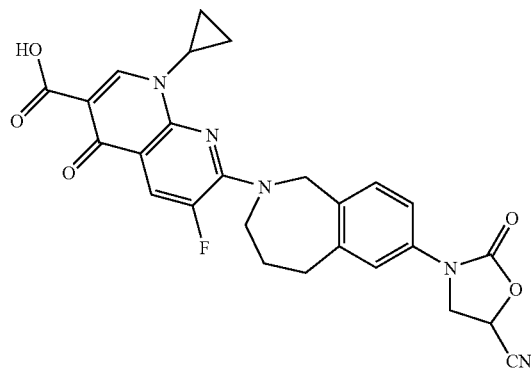

7-[7-(5-Cyano-2-oxo-oxazolidin-3-yl)-1,3,4,5-tetrahydro-benzo[c]azepin-2-yl]-1-cyclopropyl-6-fluoro-4-oxo-1,4-dihydro-[1,8]naphthyridine-3-carboxylic acid;

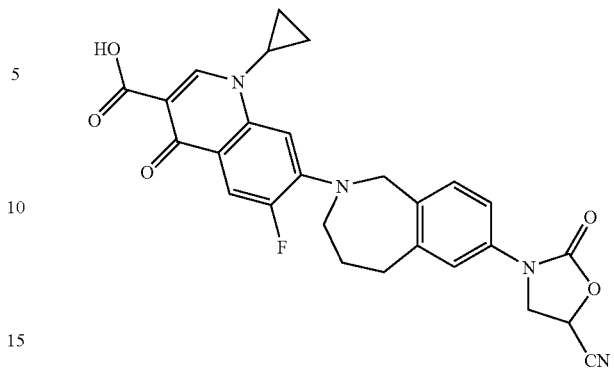

7-[7-(5-Cyano-2-oxo-oxazolidin-3-yl)-1,3,4,5-tetrahydro-benzo[c]azepin-2-yl]-1-cyclopropyl-6-fluoro-4-oxo-1,4-dihydro-quinoline-3-carboxylic acid;

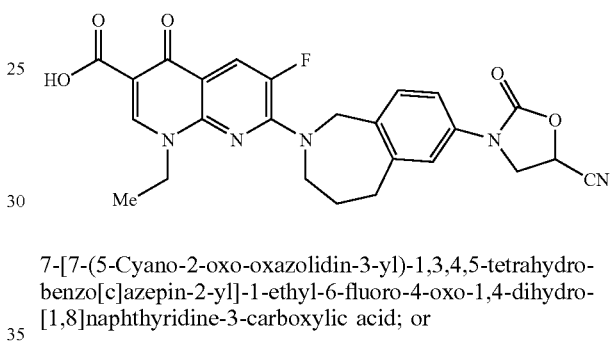

7-[7-(5-Cyano-2-oxo-oxazolidin-3-yl)-1,3,4,5-tetrahydro-benzo[c]azepin-2-yl]-1-ethyl-6-fluoro-4-oxo-1,4-dihydro-[1,8]naphthyridine-3-carboxylic acid; or

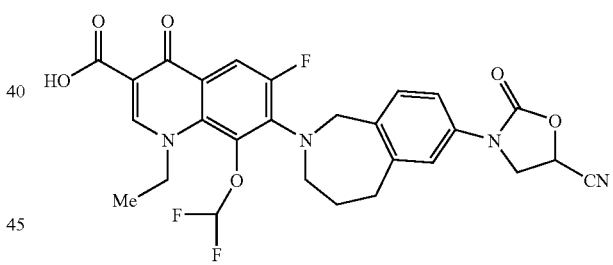

7-[7-(5-Cyano-2-oxo-oxazolidin-3-yl)-1,3,4,5-tetrahydro-benzo[c]azepin-2-yl]-8-difluoromethoxy-1-ethyl-6-fluoro-4-oxo-1,4-dihydro-quinoline-3-carboxylic acid; or a pharmaceutically acceptable salt thereof.

4. A pharmaceutical formulation comprising a compound of claim 1, 2, or 3 admixed with a pharmaceutically acceptable diluent, carrier, or excipient.

5. A method of treating a bacterial infection in a mammal, comprising administering to a mammal in need thereof an effective amount of a compound of claim 1, 2, or 3.

* * * * *